(12) United States Patent
Valentine et al.

(10) Patent No.: US 10,251,725 B2
(45) Date of Patent: Apr. 9, 2019

(54) AUTHENTICATION AND INFORMATION SYSTEM FOR REUSABLE SURGICAL INSTRUMENTS

(71) Applicant: Covidien LP, Mansfield, MA (US)

(72) Inventors: Kelly Valentine, Newington, CT (US); Thomas Windgardner, North Haven, CT (US); David McCuen, Stratford, CT (US); Michael Ingmanson, Stratford, CT (US); Gene Stellon, Burlington, CT (US); Michael Zemlock, Prospect, CT (US); Ethan Collins, Naugatuck, CT (US); Peter Collings, Shelton, CT (US)

(73) Assignee: Covidien LP, Mansfield, MA (US)

( * ) Notice: Subject to any disclaimer, the term of this patent is extended or adjusted under 35 U.S.C. 154(b) by 583 days.

(21) Appl. No.: 14/671,037

(22) Filed: Mar. 27, 2015

(65) Prior Publication Data

US 2015/0351765 A1 Dec. 10, 2015

Related U.S. Application Data

(60) Provisional application No. 62/009,456, filed on Jun. 9, 2014.

(51) Int. Cl.
*A61B 17/00* (2006.01)
*A61B 90/90* (2016.01)
(Continued)

(52) U.S. Cl.
CPC ........ *A61B 90/90* (2016.02); *A61B 17/07207* (2013.01); *A61B 90/98* (2016.02);
(Continued)

(58) Field of Classification Search
CPC ...... A61B 17/07207; A61B 2090/0807; A61B 2090/0808; A61B 2090/0811;
(Continued)

(56) References Cited

U.S. PATENT DOCUMENTS 5,157,603 A 10/1992 Scheller et al.
5,529,235 A 6/1996 Boiarski et al.
(Continued)

FOREIGN PATENT DOCUMENTS

EP 1943959 A1 7/2008
EP 2055243 A2 5/2009
(Continued)

OTHER PUBLICATIONS

European Search Report dated May 16, 2017, issued in EP Application No. 16201534.
European Search Report EP15170971.4 dated Feb. 12, 2016.

*Primary Examiner* — Chelsea E Stinson

(57) ABSTRACT

An authentication and information system for use in a surgical stapling device includes a handle assembly having a controller, the controller having at least one program and a memory, an adapter assembly, and a loading unit having a tool assembly mounted for articulation and a member for actuating articulation of the tool assembly, the loading unit having at least one chip assembly having a chip storing data indicating a position of the member when the tool assembly is in a fully articulated position.

14 Claims, 32 Drawing Sheets

(51) Int. Cl.
*A61B 17/072* (2006.01)
*A61B 90/98* (2016.01)
*A61B 17/29* (2006.01)
*A61B 90/00* (2016.01)

(52) U.S. Cl.
CPC ..... *A61B 90/06* (2016.02); *A61B 2017/00017* (2013.01); *A61B 2017/00022* (2013.01); *A61B 2017/0046* (2013.01); *A61B 2017/00393* (2013.01); *A61B 2017/00398* (2013.01); *A61B 2017/00464* (2013.01); *A61B 2017/00473* (2013.01); *A61B 2017/2927* (2013.01); *A61B 2090/064* (2016.02); *A61B 2090/0807* (2016.02); *A61B 2090/0811* (2016.02); *A61B 2090/0814* (2016.02)

(58) Field of Classification Search
CPC .... A61B 2090/0813; A61B 2090/0818; A61B 2017/2927
USPC ...................................................... 227/176.1
See application file for complete search history.

(56) References Cited

U.S. PATENT DOCUMENTS

| | | | |
|---|---|---|---|
| 7,140,528 B2 | 11/2006 | Shelton, IV | |
| 7,784,663 B2 | 8/2010 | Shelton, IV | |
| 7,823,760 B2 | 11/2010 | Zemlok et al. | |
| 7,887,530 B2 | 2/2011 | Zemlok et al. | |
| 7,922,063 B2 | 4/2011 | Zemlok et al. | |
| 8,276,801 B2 | 10/2012 | Zemlok et al. | |
| 8,308,043 B2 | 11/2012 | Bindra et al. | |
| 8,360,299 B2 | 1/2013 | Zemlok et al. | |
| 8,596,515 B2 | 12/2013 | Okoniewski | |
| 8,708,211 B2 | 4/2014 | Zemlok et al. | |
| 8,733,614 B2 | 5/2014 | Ross et al. | |
| 8,800,837 B2 * | 8/2014 | Zemlok | A61B 17/07207 227/175.1 |
| 8,806,973 B2 | 8/2014 | Ross et al. | |
| 9,808,246 B2 * | 11/2017 | Shelton, IV | A61B 17/068 |
| 2005/0020909 A1 | 1/2005 | Moctezuma de la Barrera et al. | |
| 2006/0212069 A1 * | 9/2006 | Shelton, IV | A61B 17/072 606/205 |
| 2008/0255413 A1 | 10/2008 | Zemlok et al. | |
| 2008/0300580 A1 * | 12/2008 | Shelton, IV | A61B 17/07207 606/1 |
| 2008/0312687 A1 | 12/2008 | Blier | |
| 2009/0054908 A1 | 2/2009 | Zand et al. | |
| 2009/0090763 A1 | 4/2009 | Zemlok et al. | |
| 2009/0209979 A1 * | 8/2009 | Yates | A61B 17/07207 606/143 |
| 2010/0096435 A1 | 4/2010 | Fuchs et al. | |
| 2011/0017801 A1 | 1/2011 | Zemlok et al. | |
| 2011/0022032 A1 * | 1/2011 | Zemlok | A61B 17/07207 606/1 |
| 2011/0295269 A1 * | 12/2011 | Swensgard | A61B 17/068 606/130 |
| 2011/0309128 A1 | 12/2011 | Okoniewski | |
| 2012/0228358 A1 | 9/2012 | Zemlok et al. | |
| 2012/0232540 A1 | 9/2012 | Baur et al. | |
| 2013/0008935 A1 | 1/2013 | Brusaw et al. | |
| 2013/0168431 A1 | 7/2013 | Zemlok et al. | |
| 2013/0214025 A1 | 8/2013 | Zemlok et al. | |
| 2014/0008412 A1 | 1/2014 | Zemlok et al. | |
| 2014/0110455 A1 | 4/2014 | Ingmanson et al. | |

FOREIGN PATENT DOCUMENTS

| | | |
|---|---|---|
| EP | 2377472 A1 | 10/2011 |
| EP | 2486860 A2 | 8/2012 |
| EP | 2586383 A2 | 5/2013 |
| EP | 2722010 A1 | 4/2014 |
| EP | 2772210 A2 | 9/2014 |
| EP | 2839795 A1 | 2/2015 |
| EP | 2851009 A1 | 3/2015 |
| EP | 2881044 A1 | 6/2015 |
| EP | 2923649 A1 | 9/2015 |
| EP | 2923653 A2 | 9/2015 |

* cited by examiner

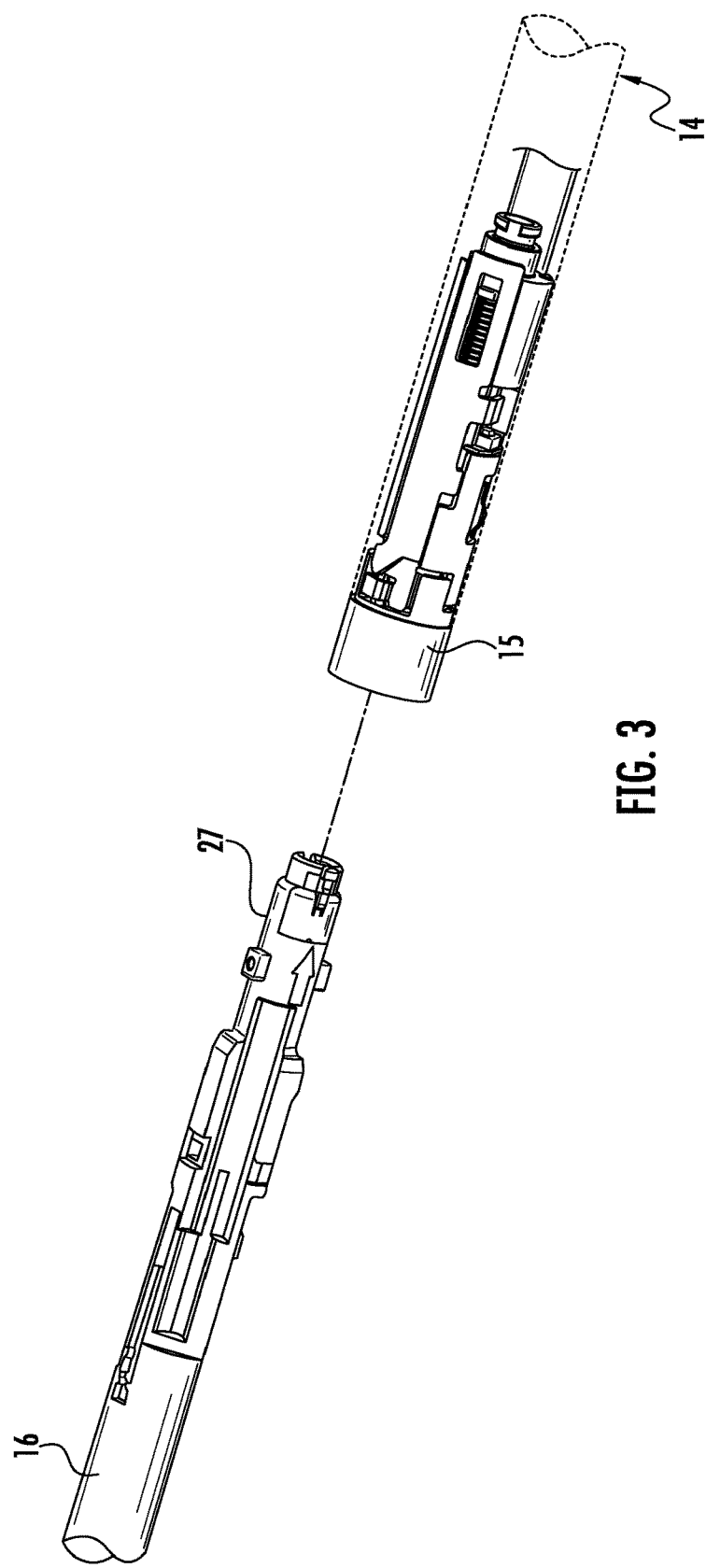

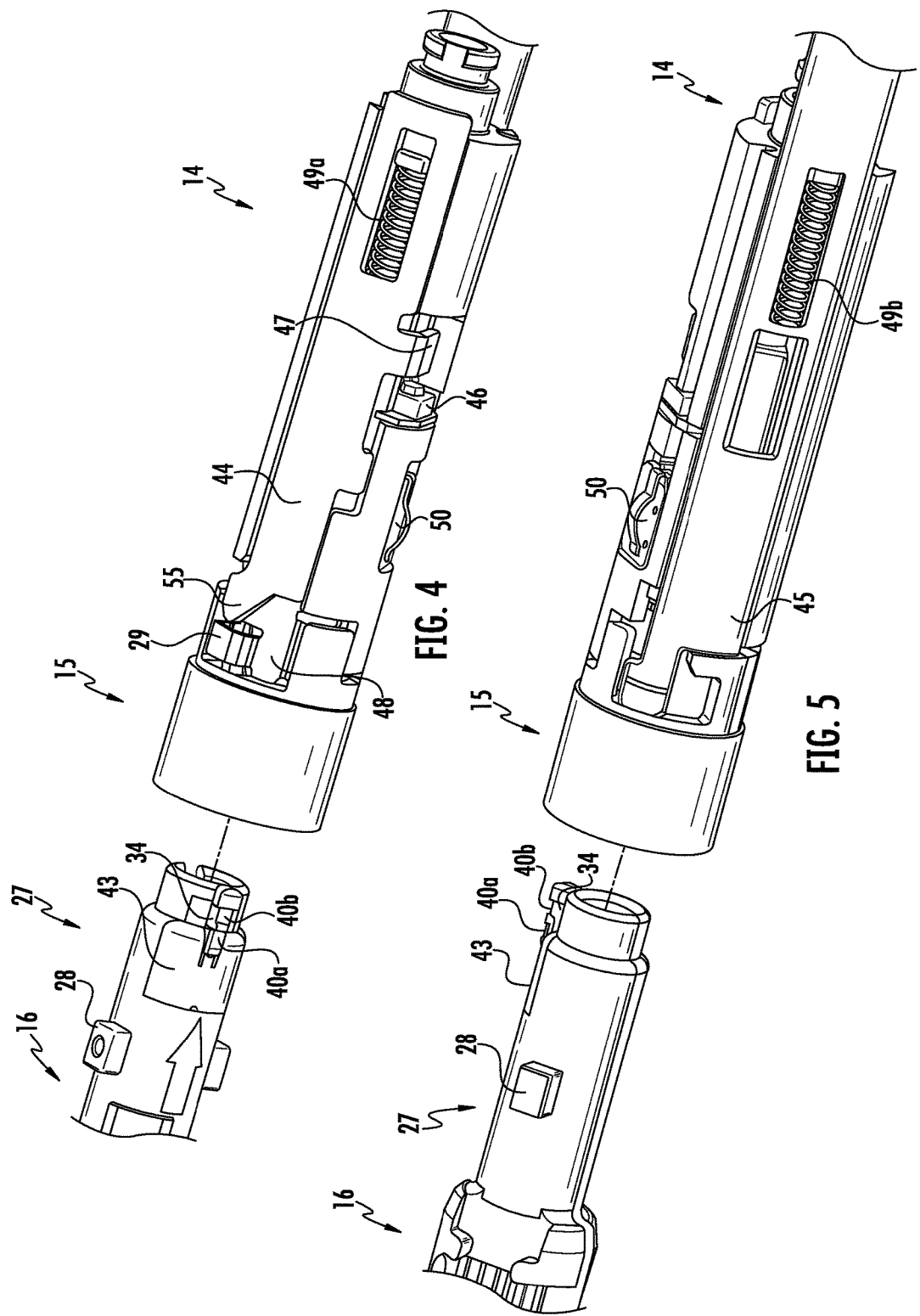

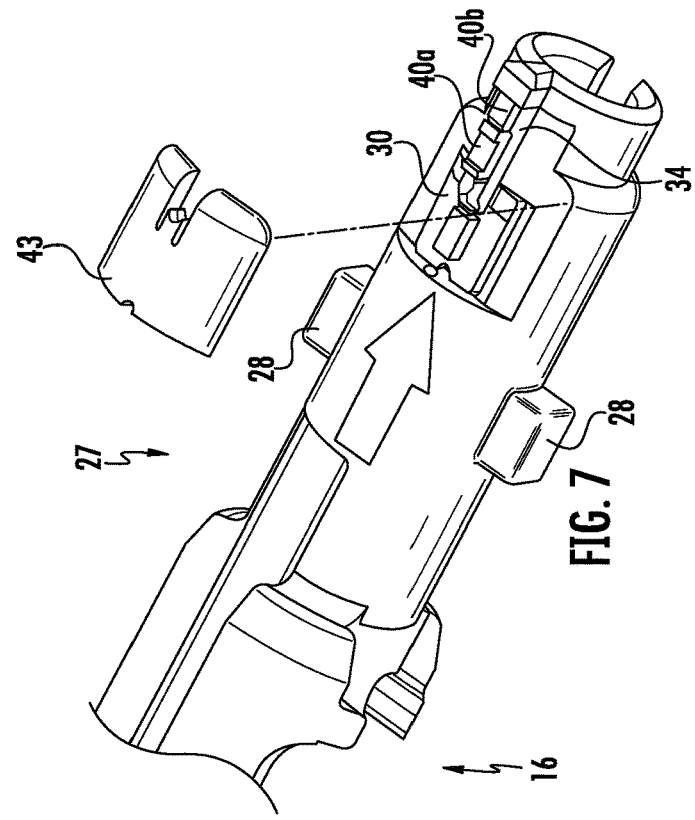
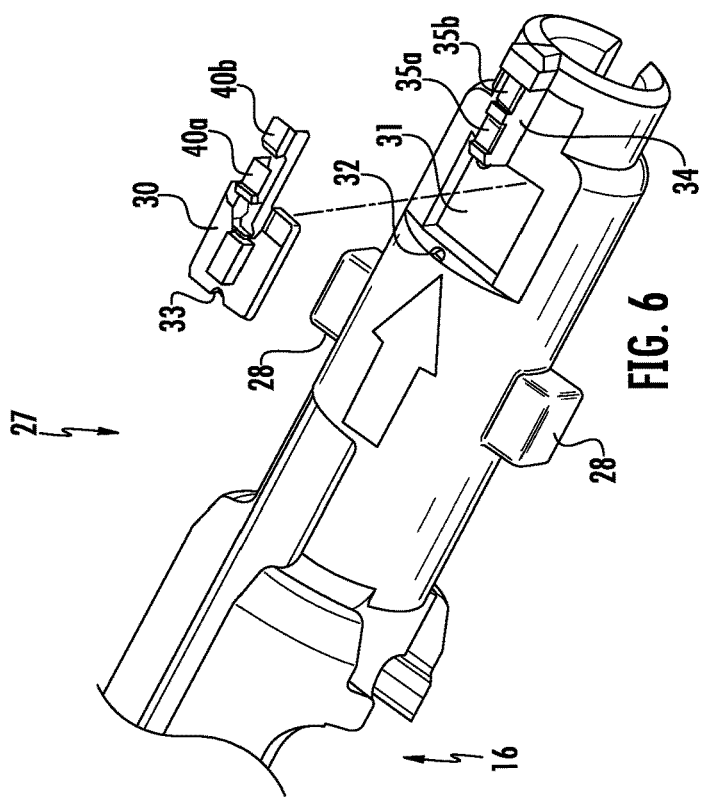

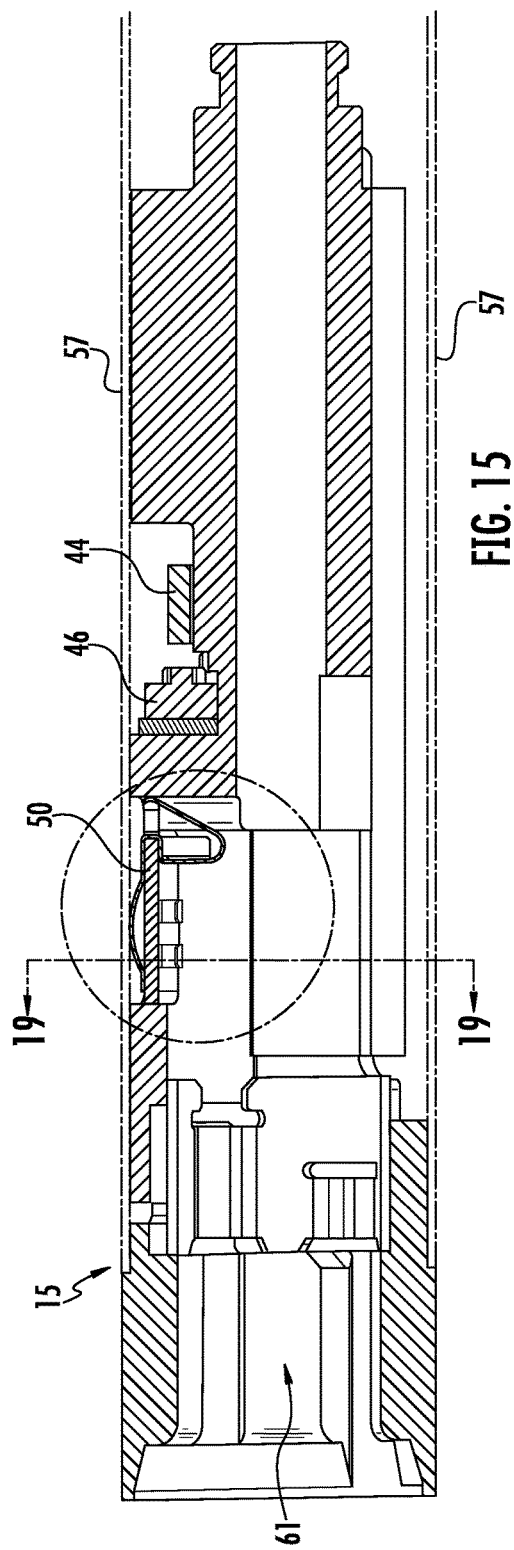
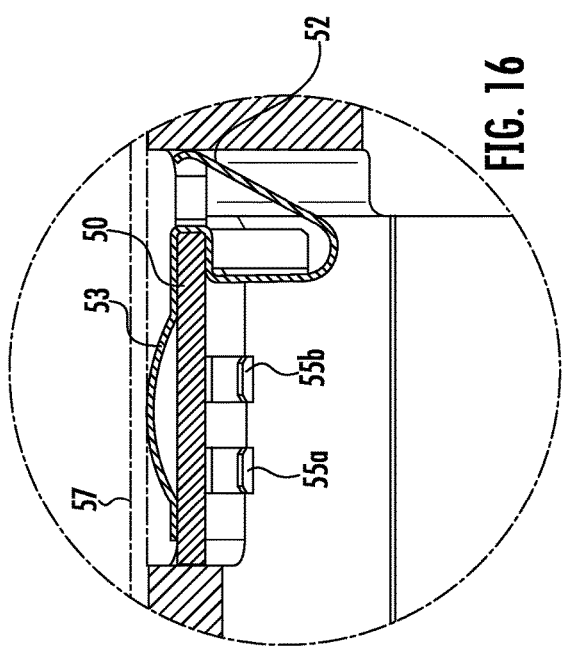

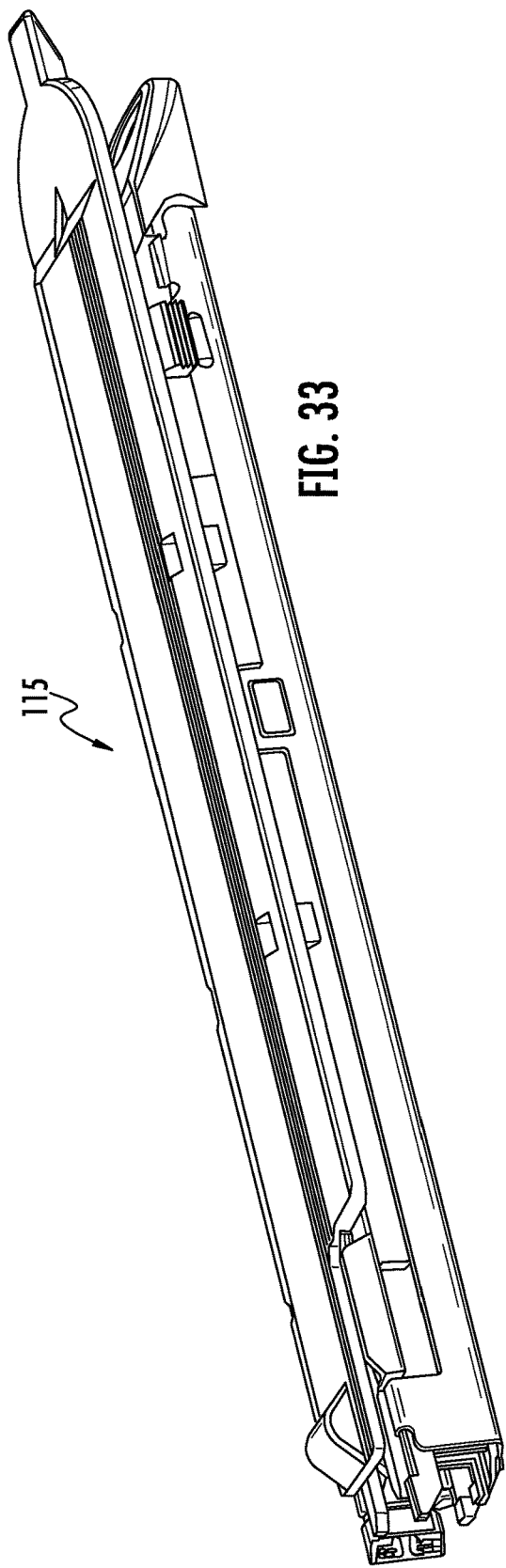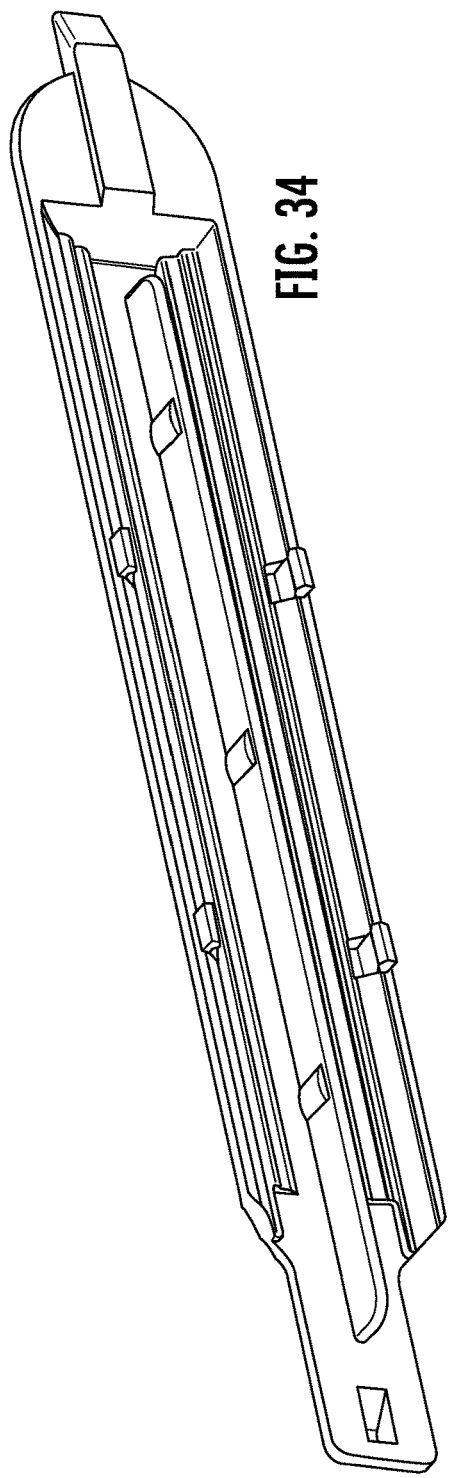

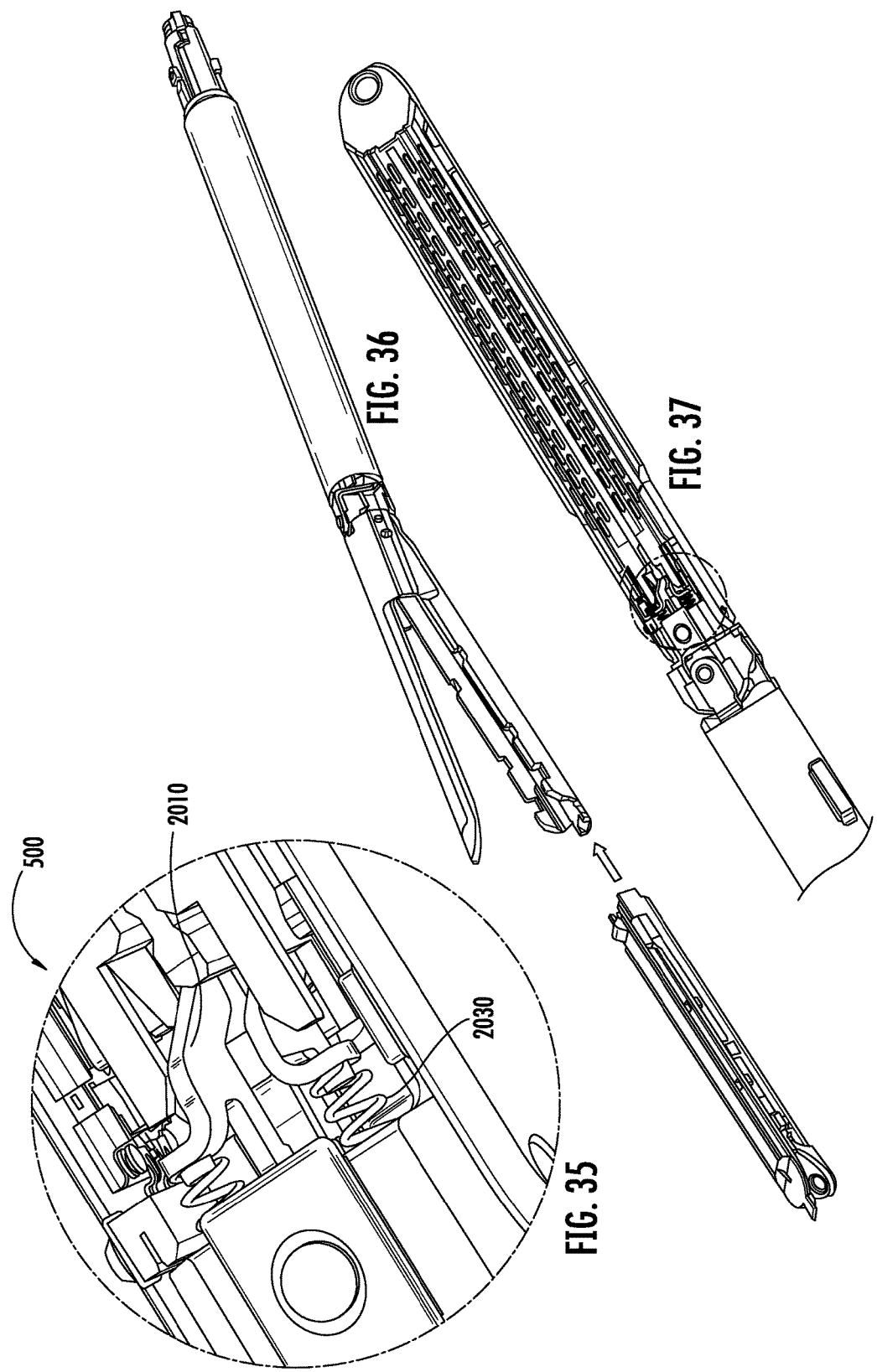

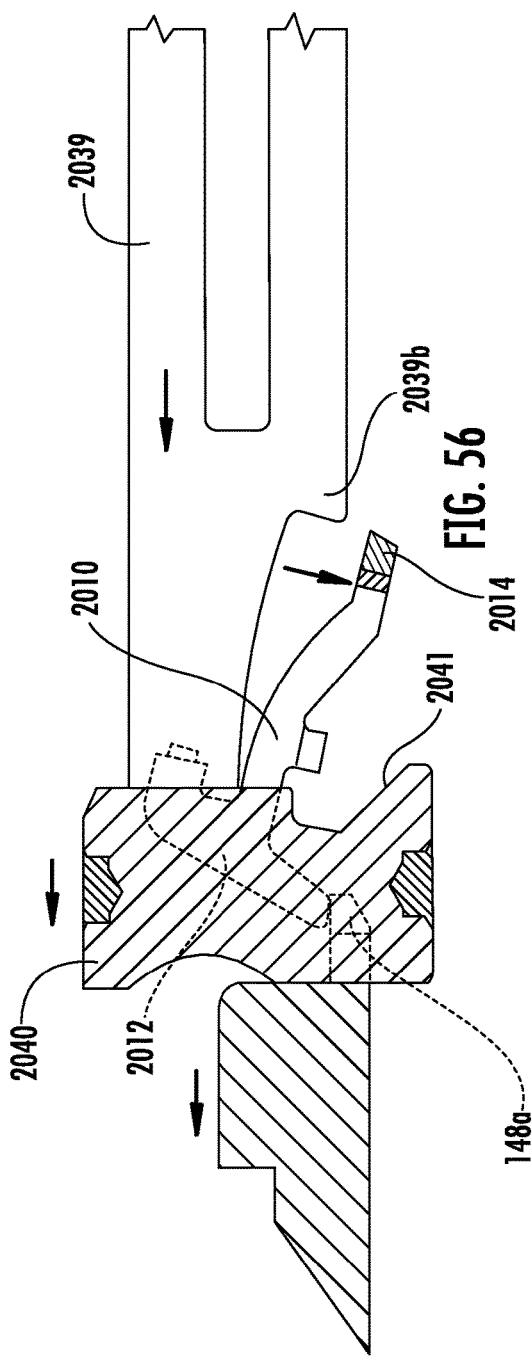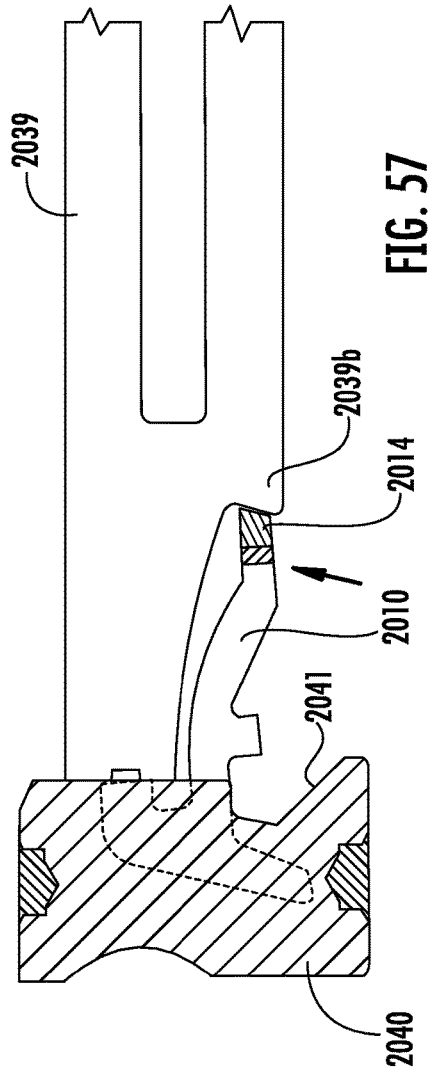

AUTHENTICATION AND INFORMATION SYSTEM FOR REUSABLE SURGICAL INSTRUMENTS

CROSS-REFERENCE TO RELATED APPLICATIONS

This application claims the benefit of and priority to U.S. Provisional Patent Application No. 62/009,456, filed Jun. 9, 2014, the entire disclosure of which is incorporated by reference herein.

BACKGROUND

Technical Field

The present disclosure relates to surgical instruments having a reusable handle and removable and replaceable components, such as a disposable or replaceable loading unit. The present disclosure also relates to an authentication system for the components and/or handle assembly for use in a surgical stapling system.

Description of Related Art

Powered surgical instruments for use in endoscopic procedures are known. Typically, such instruments include a reusable handle assembly, and a replaceable and generally disposable component sometimes referred to as single use loading unit or SULU. An adapter assembly connects the loading unit, which can include an end effector for interacting with tissue, to the handle assembly. In the case of a surgical stapler, the end effector can include a replaceable cartridge that is changed after each firing of the surgical stapler. To reduce costs and shorten procedure times, the handle assemblies are generally configured for use with a variety of loading units and/or assemblies of various configurations for use on tissue having different properties, e.g., thickness and density. For example, the different loading units may have staples of different sizes and/or the staples may be arranged in different configurations. To ensure the handle assembly is programmed to operate with the attached loading unit, some loading units are provided with an integrated circuit, also known as a chip, that communicates with the handle assembly to identify the configuration of the loading unit. This arrangement enables the configuration of the loading unit to be automatically conveyed to the handle assembly upon attachment of the loading unit to the adapter assembly, thereby eliminating user error or incompatibility that may be experienced when switching between loading units with different configurations.

Surgical staplers are commonly used for stapling tissue within a body cavity where the end effector is likely to come in contact with fluids, e.g., blood, bile, and/or irrigation solutions. If the interconnections between the chip and the handle assembly are compromised, the chip could malfunction or data communications between the loading unit and the handle assembly could be disrupted, rendering the surgical stapler unstable or inoperable.

A stapling instrument configured to increase the reliability of communications between the disposable loading unit and the handle assembly would be a welcome advance. Provision of an authentication system for components in a surgical system is also desirable. Systems for enabling a variety of components to be used with surgical handle assemblies is another desirable aspect.

SUMMARY

In an aspect of the present disclosure, a surgical system comprises a handle assembly having a controller, the controller having at least one program and a memory, an adapter assembly, and a loading unit having a tool assembly mounted for articulation and a member for actuating articulation of the tool assembly, the loading unit having at least one chip assembly having a chip storing data indicating a position of the member when the tool assembly is in a fully articulated position.

The chip can have data indicating a type of loading unit, the memory of the controller having a current profile for the type of loading unit. The chip can store data indicating a length of the tool assembly and/or data indicating whether or not the tool assembly articulates. The controller can read the data and not drive an articulation link in the adapter assembly and/or loading unit if the data indicated that the loading unit does not articulate.

The controller can monitor current from a motor during operation of the loading unit.

The loading unit may include a removable and replaceable staple cartridge assembly. The removable and replaceable staple cartridge assembly can have a chip assembly including a chip storing data indicating whether or not the staple cartridge assembly has been fired.

The controller can monitor the position of the member and stores data concerning movement of the member in the memory. The number of times the tool assembly has been articulated can be saved in the memory. The memory can have data indicating the position of the member when the tool assembly is in a fully articulated position.

In certain aspects of the present disclosure, a surgical system comprises a handle assembly having a controller, the controller having a memory and at least one program, the handle assembly having at least one button, an adapter assembly, and a loading unit, the controller assigning a function to the at least one button. The function can be articulation, or clamping tissue, or be selected from the group consisting of clamping tissue, firing staples and cutting tissue, and combinations thereof.

The function assigned can depend on a type of the loading unit. The loading unit can be a circular stapling loading unit, a linear surgical stapling loading unit, or other type of loading unit. The loading unit may include a dynamic clamping member. The dynamic clamping member can perform at least one of clamp tissue, fires staples, and cut tissue.

In another aspect of the present disclosure, a surgical system comprises a handle assembly having a controller, the controller having a memory and at least one program an adapter assembly, and a loading unit, the memory of the controller storing a current profile associated with the loading unit. The controller can store information from sensors, encoders, or both. The controller can compare the current profile to information from the sensors, encoders, or both. The controller can read a type for the loading unit from a chip on the loading unit. The controller can select a current profile from a plurality of current profiles stored in the controller.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3 is a view of a proximal end of a loading unit and a distal end of an adapter assembly of the surgical stapling device shown in FIG. 1;

FIG. 4 is an enlarged view of the proximal end of the loading unit and the distal end of the adapter assembly shown in FIG. 3;

FIG. 5 is another enlarged view of the proximal end of the loading unit and the distal end of the adapter assembly shown in FIG. 3;

FIG. 6 is an enlarged, exploded view of the proximal end of the loading unit shown in FIG. 3 with the loading unit and authentication board separated;

FIG. 7 is an enlarged, partially-exploded view of the proximal end of the loading unit shown in FIG. 3 with the authentication board cover separated from the loading unit;

FIG. 15 is a cross-sectional, side view of the adapter assembly shown in FIG. 3 showing the adapter assembly separated from the loading unit;

FIG. 16 is an enlarged view of the indicated area shown in FIG. 15 showing the adapter board separated from the authentication board;

FIG. 33 is a top perspective view of the staple cartridge assembly of FIG. 32, with a shipping wedge;

FIG. 34 is a bottom perspective view of the shipping wedge of FIG. 33;

FIG. 35 is a detailed perspective view of a lockout assembly in accordance with embodiments of the present disclosure;

FIG. 36 is a perspective view of the loading unit of FIG. 23 showing the staple cartridge assembly;

FIG. 37 is a top view of the loading unit with the anvil and shipping wedge removed;

FIG. 56 is a side view of the drive beam, dynamic clamping member, and sled;

FIG. 57 is a side view of the drive beam, dynamic clamping member, and sled, with the drive beam and dynamic clamping member advanced;

DETAILED DESCRIPTION

Figure 1:
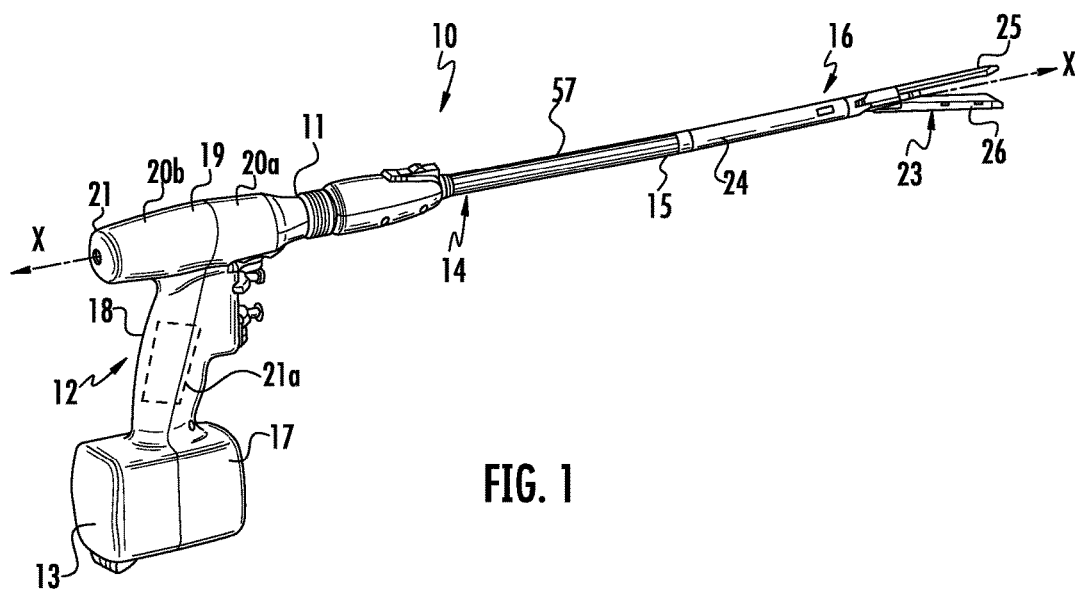
FIG. 1 is a perspective view of a surgical stapling device for use with a chip assembly according to embodiments of the present disclosure.

Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As is common in the art, the term "proximal" refers to that part or component closer to the user or operator, i.e. surgeon or clinician, while the term "distal" refers to that part or component further away from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions. Embodiments of the presently disclosed chip assembly will now be described in detail with reference to the drawings in which like reference numerals designate identical or corresponding elements in each of the several views. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Figure 2:
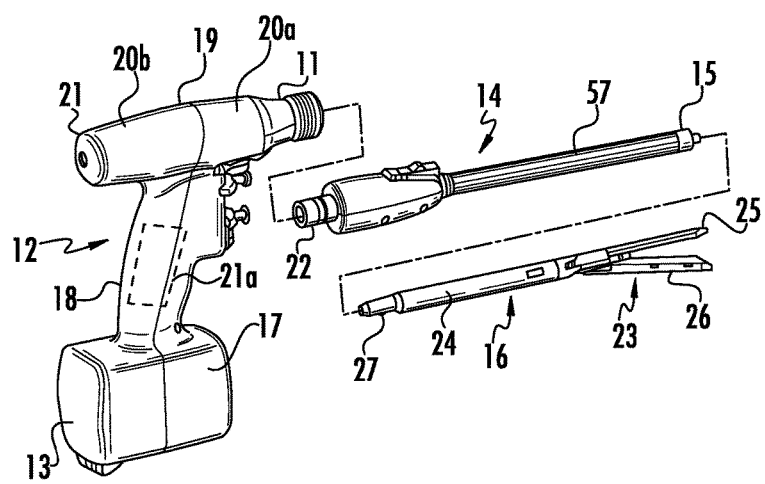
FIG. 2 is a perspective view of the surgical stapling device of FIG. 1 showing the handle assembly, adapter assembly, and loading unit in a separated configuration.

With reference initially to FIGS. 1 and 2, a surgical stapling instrument including an authentication system according to the present disclosure is shown generally as stapler 10. Stapler 10 includes a handle assembly 12, an adapter assembly 14 extending distally from handle assembly 12, and a loading unit 16 selectively secured to a distal end of adapter assembly 14. A detailed description of handle assembly 12, adapter assembly 14, and loading unit 16 is provided in commonly-owned U.S. Patent Appl. Publ. No. 2012/0089131, the contents of which is incorporated herein by reference in its entirety.

Handle assembly 12 includes a lower housing portion 17, an intermediate housing portion 18 extending from and/or supported on lower housing portion 17, and an upper housing portion 19 extending from and/or supported on intermediate housing portion 18. Intermediate housing portion 18 and upper housing portion 19 are separated into a distal half-section 20a that is integrally formed with, and extends from, the lower housing portion 17, and a proximal half-section 20b joined to distal half-section 20a by any suitable manner of attachment, such as without limitation, ultrasonic welding and/or a plurality of fasteners. When joined, distal and proximal half-sections 20a, 20b form a handle housing 21 defining a cavity therein which houses a circuit board that includes a controller 21a, and a drive mechanism (not shown).

Lower housing portion 17 includes a door 13 pivotally connected thereto for accessing a cavity formed in lower housing portion 17 for retaining a battery (not shown) therein. It is contemplated that stapler 10 may be powered by any number of power sources, such as, for example and without limitation, a fuel cell, a power cord connected to an external power source, and so forth.

Adapter assembly 14 includes a drive coupler 22 at a proximal end thereof and a loading unit coupler 15 at a distal end thereof. Distal half-section 20a of upper housing portion 19 defines a nose or connecting portion 11 configured to operably receive drive coupler 22 of adapter assembly 14. Loading unit 16 includes an adapter coupler 27 configured to operably receive loading unit coupler 15 of adapter assembly 14.

Upper housing portion 19 of handle housing 21 encloses a drive mechanism (not shown) configured to drive shafts and/or gear components (not shown) in order to perform the various operations of stapler 10. In particular, the drive mechanism is configured to drive shafts and/or gear components in order to selectively move a tool assembly or end effector 23 of loading unit 16 relative to a proximal body portion 24 of loading unit 16, to rotate loading unit 16 about a longitudinal axis "X-X" (FIG. 1) relative to handle housing 21, to move an anvil assembly 25 relative to cartridge assembly 26 of loading unit 16, and/or to fire a stapling and cutting cartridge within cartridge assembly 26 of loading unit 16.

The loading unit 16 shown in the FIGS. 1-21 is a linear surgical stapling loading unit. The loading unit includes a stapling anvil with recesses for forming surgical staples that are driven against it by operation of the loading unit in the surgical system. A staple cartridge houses the surgical staples, as well as the staple firing and/or driving assembly. The staple firing and/or driving assembly is known. One such assembly is described in U.S. Pat. Nos. 8,256,656 and 7,044,353, the entire disclosures of which are hereby incorporated by reference herein. The drive assembly includes an elongated drive beam having a knife blade. The drive beam pushes an actuation sled having wedge shaped surfaces for interacting with pushers. The pushers support the staples and have camming surfaces that the sled wedge shaped surfaces slide against, driving the pushers upwardly while the sled is advanced in a longitudinal fashion through the staple cartridge.

It is contemplated that the loading unit has jaw members for supporting the anvil and the staple cartridge respectively. The anvil jaw member and staple cartridge jaw member can be approximated to clamp tissue therebetween. It is also contemplated that the end effector can articulate or pivot off axis from the longitudinal axis defined by the proximal body portion 24.

It is contemplated that the loading unit can be a circular surgical stapling unit, other types of stapling units, or other types of surgical end effectors, such as electrocautery, ablation, ultrasonic, etc.

With reference to FIGS. 3, 4, and 5, loading unit coupler 15 of adapter assembly 14 is configured to operably engage adapter coupler 27 of loading unit 16 via a push and twist or bayonet-type arrangement. Adapter coupler 27 includes one or more bayonet lugs 28 that are configured to mate with corresponding one or more bayonet channels 29 defined in a bayonet collar 48 provided by loading unit coupler 15 of adapter assembly 14. A short link member 44 and a load link member 45 are longitudinally disposed within adapter assembly 14 and are configured to translate longitudinally (e.g., distally and proximally) during operation of stapler 10.

A cam 55 disposed at a distal end of short link member 44 is urged distally against a bayonet channel 29 by spring 49a. To engage loading unit 16 with adapter assembly 14, adapter coupler 27 of loading unit 16 is inserted into loading unit coupler 15 of adapter assembly 14 and rotated. In turn, bayonet collar 48 rotates cooperatively with adapter coupler 27. As bayonet collar 48 rotates, cam 55 rides off bayonet channel 29, causing short link member 44 to translate distally, which, in turn, causes a switch tab 47 formed in short link member 44 to actuate switch 46. Switch 46 is in operative electrical communication with the controller 21a and is configured to convey thereto the engagement status between loading unit 16 and adapter assembly 14.

Figure 11:
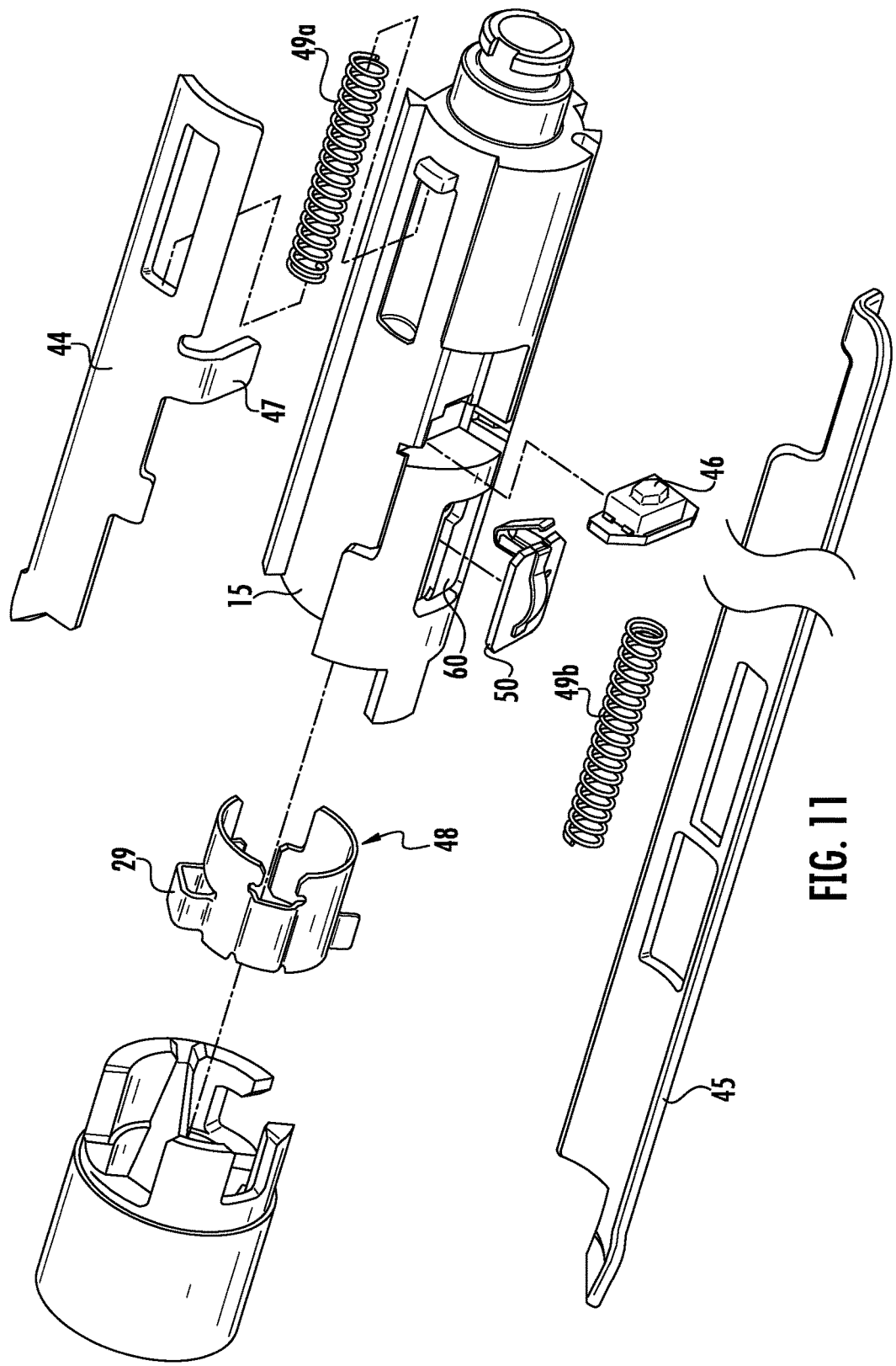
FIG. 11 is an enlarged, exploded view of the distal end of the adapter assembly shown in FIG. 3 with the adapter assembly and adapter board separated.
Figure 12:
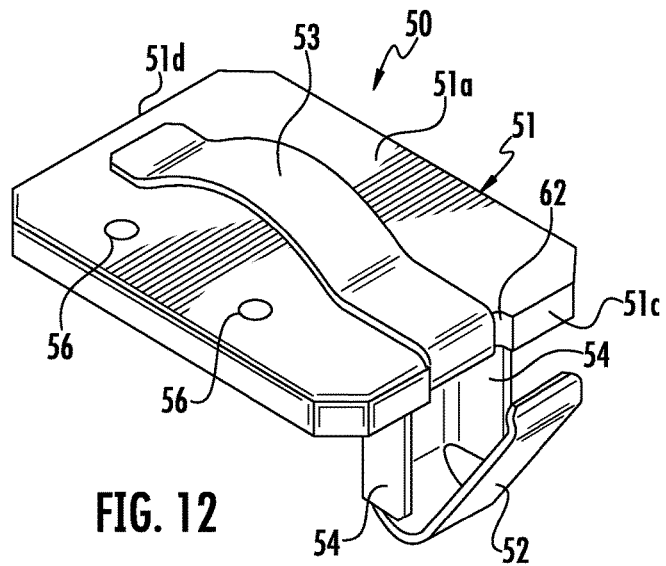
FIG. 12 is an enlarged view of the adapter board shown in FIG. 11.
Figure 13:
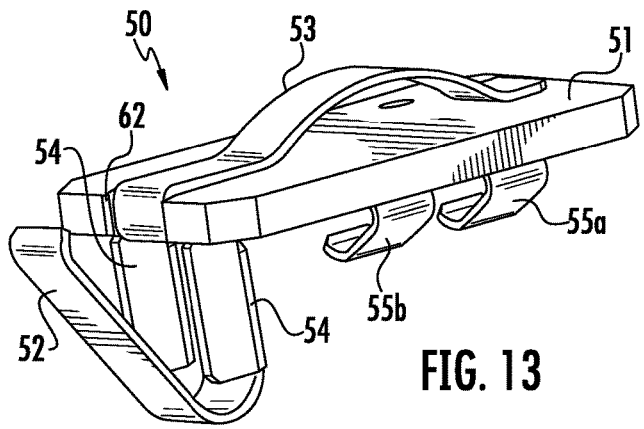
FIG. 13 is another enlarged view of the adapter board shown in FIG. 11.
Figure 14:
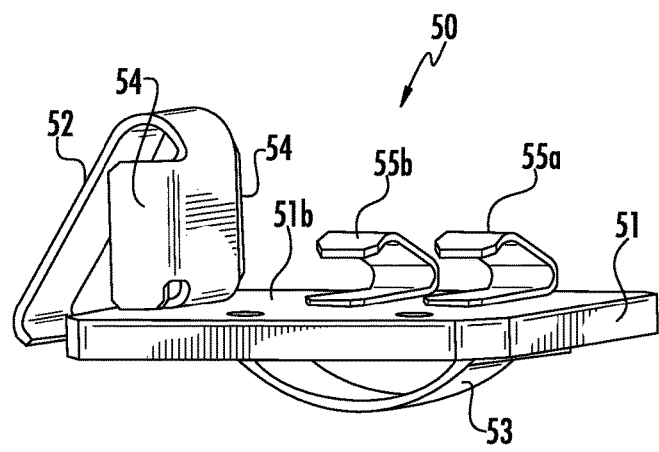
FIG. 14 is yet another enlarged view of the adapter board shown in FIG. 11.
Figure 17:
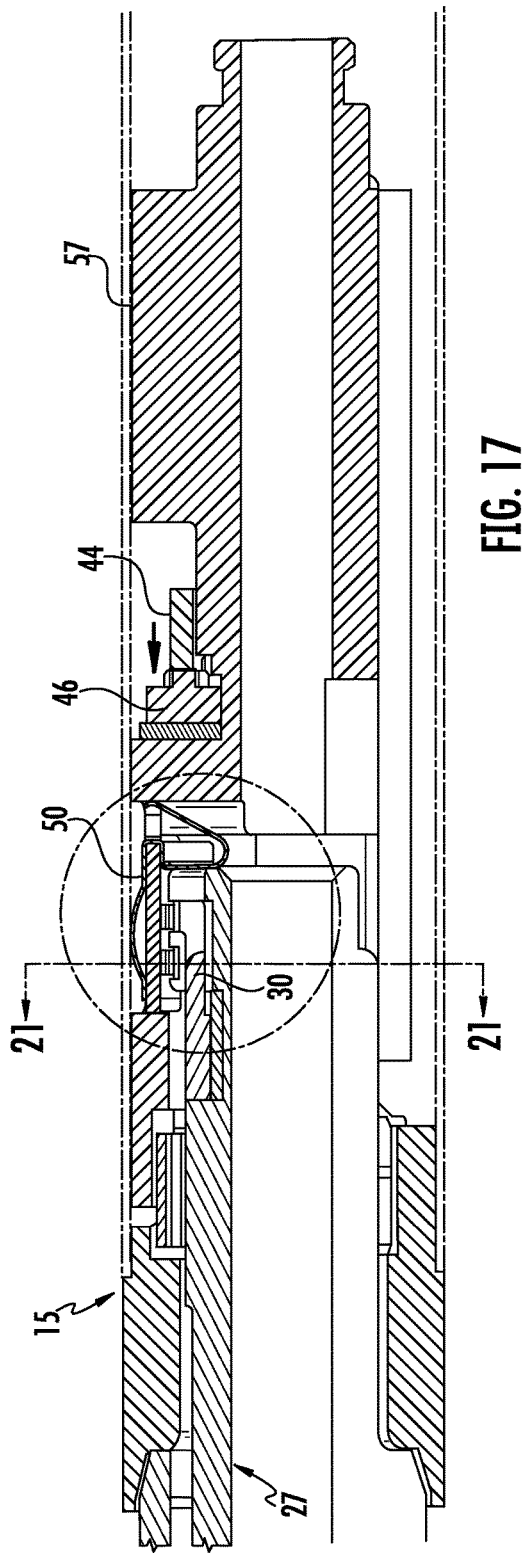
FIG. 17 is a cross-sectional, side view of the adapter assembly shown in FIG. 3 showing the adapter assembly engaged with the loading unit.
Figure 18:
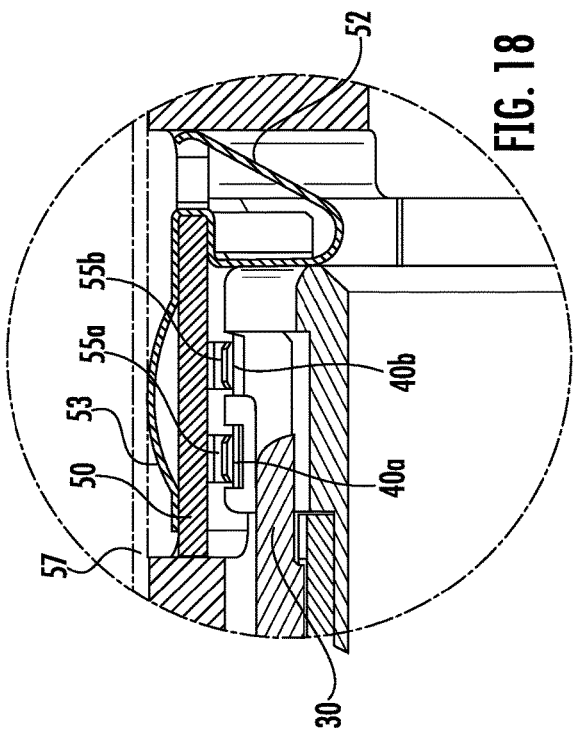
FIG. 18 is an enlarged view of the indicated area shown in FIG. 17 showing the adapter board engaged with the authentication board.

Turning now to FIGS. 6-10, adapter coupler 27 of loading unit 16 includes an authentication board assembly 30 that is configured to be securely mounted within a recess 31 defined in adapter coupler 27. Authentication board assembly 30 is positioned within adapter coupler 27 such that when loading unit 16 is secured to adapter assembly 14, authentication board assembly 30 engages an adapter board assembly 50 mounted within loading unit coupler 15 of the adapter assembly (FIG. 11). In more detail, authentication board 30 includes a circuit board 37, a pair of contact members 40a, 40b (collectively, contact members 40) and a chip 36. Circuit board 37 defines a substantially planar elongated member configured to be securely received within recess 31 defined by adapter coupler 27. Chip 36 is in electrical communication with contact members 40. A distal end 37a of circuit board 37 supports chip 36, and a proximal end 37b of circuit board 37 supports contact members 40. Distal end 37a of circuit board 37 includes an alignment notch 33 defined therein that is configured to engage a corresponding alignment nub 32 provided at a distal end of recess 31 to ensure secure and accurate positioning of authentication board assembly 30 within adapter coupler 27.

Chip 36 includes any chip capable of storing the specifications of loading unit 16, such as, without limitation, cartridge size, staple arrangement, staple length, clamp-up distance, date of manufacture, expiration date, compatibility characteristics, a unique identifier (e.g., a serial number), and/or number of uses, and transmitting the specifications to handle assembly 12. In some embodiments, chip 36 includes an erasable programmable read only memory ("EPROM") chip. In this manner, the handle assembly 12 may adjust the firing forces, firing stroke, and/or other operational characteristics thereof in accordance with the specifications of loading unit 16 that are transmitted from chip 36. It is further envisioned that chip 36 may include write capabilities which allow handle assembly 12 to communicate to chip 36 that the associated loading unit 16 has been used, which can prevent reloading or reuse of an expended reload assembly, or any other unauthorized use.

In some embodiments, chip 36 includes a secure authentication chip, such as, without limitation, a DS28E15 DeepCover™ Secure Authenticator with 1-Wire SHA-256 and 512-Bit User EEPROM, manufactured by Maxim Integrated™ of San Jose, Calif. In these embodiments, the contents of chip 36, and the communications between chip 36 and handle assembly 12, are encrypted to prevent unauthorized access. In this manner, the use of low-quality counterfeit, re-manufactured, or "knock-off" loading units is effectively discouraged, which, in turn, reduces risk to patients by ensuring that only fresh, authentic loading units 16 are used during surgical procedures. In addition, the likelihood that medical facilities and/or surgeons may unwittingly use counterfeit loading units is greatly curtailed, thus reducing the overall costs to society for delivering medical services. In some embodiments, chip 36 utilizes a "1-wire" communications interface whereby a single signal conductor is employed, together with a ground conductor, for bidirectional serial communications between chip 36 and handle assembly 12.

Contact assembly 38 (FIGS. 9, 10) includes a short contact arm 41 and a long contact arm 42 joined by a contact base 59, and having a generally elongated u-shaped configuration. Short contact arm 41 includes a first contact member 40a orthogonally disposed and fixed to an upper portion of a proximal end thereof. Long contact arm 42 includes a second contact member 40b orthogonally disposed and fixed to an upper portion of a proximal end thereof. Short and long contact arms 41, 42 each include a solder tab 39 orthogonally disposed and fixed to a lower portion of a distal end thereof. Solder tabs 39 are electromechanically joined to a proximal end 37b of circuit board 37 by, e.g., soldering, electrically conductive adhesive, and/or other suitable technique.

Figure 8:
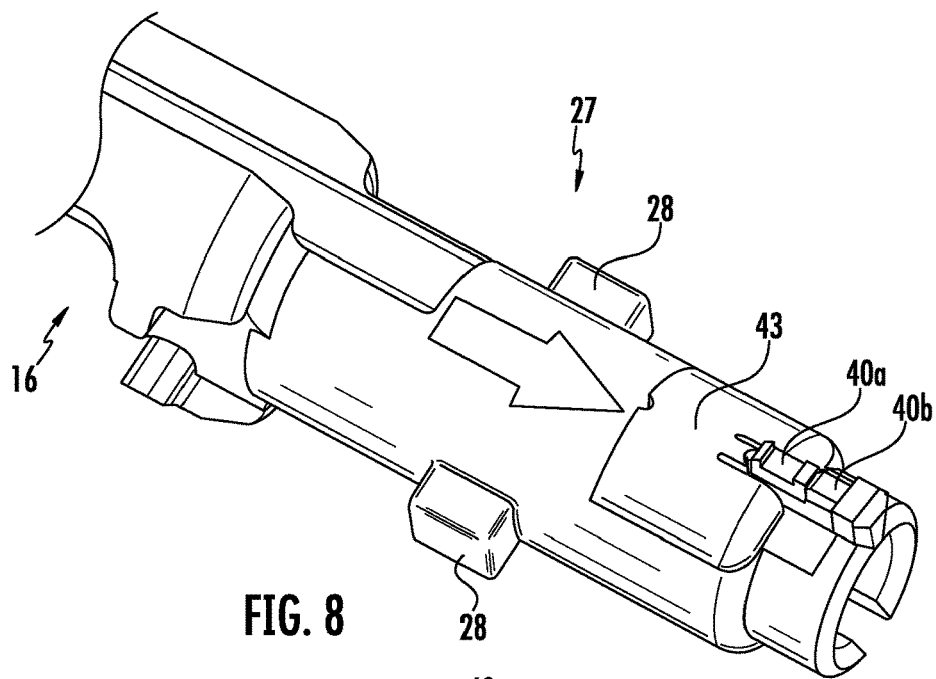
FIG. 8 is an enlarged view of the proximal end of the loading unit shown in FIG. 3.
Figure 9:
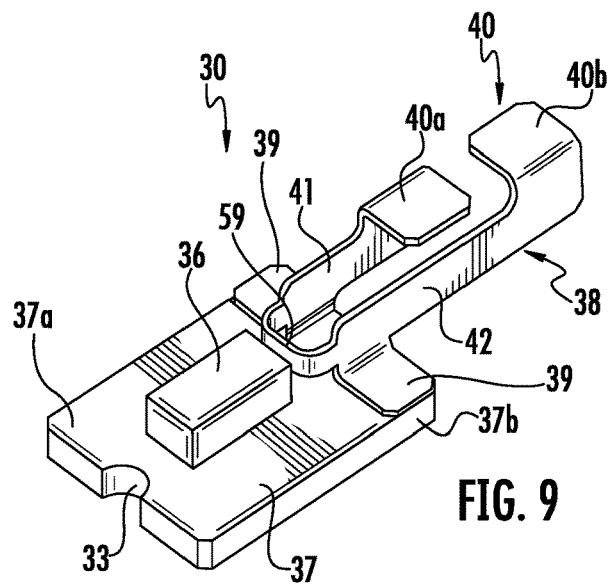
FIG. 9 is a perspective view of an authentication board assembly according to an embodiment of the present disclosure.
Figure 10:
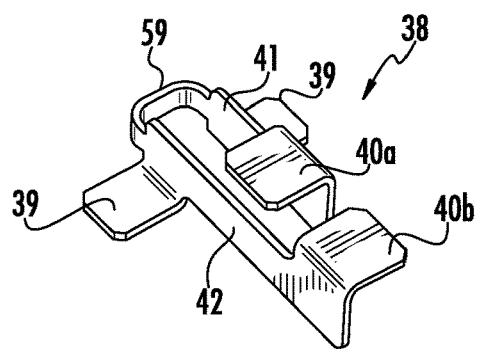
FIG. 10 is a perspective view of an authentication board contact.

Adapter coupler 27 includes a raised contact support 34 extending radially from a proximal end thereof and includes a pair of cradles 35a, 35b defined therein that are configured to receive first contact member 40a and second contact member 40b, respectively, when authentication board assembly 30 is positioned within recess 31 of adapter coupler 27. A cover 43 is configured to enclose and retain authentication board assembly 30 within recess 31 of adapter coupler 27 (FIGS. 7 and 8).

In some embodiments, short contact arm 41 and first contact member 40a are electrically insulated from long contact arm 42 and second contact member 40b by contact base 59. In these embodiments, each of short contact arm 41 and long contact arm 42 carries a separate circuit, e.g., short contact arm 41 carries signal and long contact arm 42 carries ground. In other embodiments, short contact arm 41 and first contact member 40a are electrically joined with long contact arm 42 and second contact member 40b. In these embodiments, short contact arm 41 and long contact arm 42 operate in a bifurcated or redundant mode to carry a signal circuit, while the ground circuit is carried through other electrically conductive components of loading unit 16, adapter unit 14, and/or handle assembly 12.

As mentioned above, authentication board assembly 30 is configured to engage adapter board assembly 50 mounted within loading unit coupler 15 when loading unit 16 is secured to adapter assembly 14. With reference now to FIGS. 11-14, loading unit coupler 15 includes an adapter board assembly 50 that is configured to be floatingly mounted within a pocket 60 defined in loading unit coupler 15. Adapter board assembly 50 is positioned within loading unit coupler 15 such that when loading unit 16 is secured to adapter assembly 14, adapter board assembly 50 engages authentication board assembly 30.

Adapter board assembly 50 includes a circuit board 51 having a pair of contact members 55a, 55b (collectively, contact members 55) fixed thereto and in operable communication with handle assembly 12. In the illustrated embodiment, contact members 55a, 55b are arranged for effective engagement in a transverse direction, e.g., transverse to the longitudinal axis "X-X" of stapler 10, to accommodate the rotational coupling of loading unit 16 and adapter assembly 14 as described herein.

Circuit board 51 includes an upper surface 51a, a lower surface 51b, a proximal end 51c, and a distal end 51d. Circuit board 51 defines a substantially planar elongated member configured to be resiliently or floatingly received within pocket 60 defined by loading unit coupler 15. A spring clip 52 is fixed to a proximal end 51c of circuit board 51 and is configured to support adapter board assembly 50 within pocket 60. Spring clip 52 includes a pair of spring supports 54 having a wing-like configuration that are configured prevent spring clip 52 from over-extension and to provide stiffness thereto. Adapter board assembly 50 includes a spring 53 having a broad, curvate u-shaped profile disposed on an upper surface 51a of circuit board 51. In some embodiments, spring clip 52 and spring 53 may be integrally formed. Spring clip 52 and/or spring 53 may be positively aligned and/or supported by a notch 62 defined in proximal end 51c of circuit board 51. Circuit board 51 includes one or more through holes 56 defined therein that may be utilized to form a conductive pathway between upper surface 51a and lower surface 51b of circuit board 51.

When adapter board assembly 50 is mounted within pocket 60, spring 53 bears against outer tube 57 of adapter assembly 14 (FIGS. 15, 16). In use, adapter board 50 is spring-biased towards authentication board assembly 30 by spring 53 and by side spring clip 52 such that, upon joining loading unit 16 and adapter assembly 14, any manufacturing tolerances between loading unit 16 and adapter assembly 14 are compensated for by engagement of the floating spring mount of adapter board 50 within pocket 60. Alternative methods of biasing in addition to the spring 53 are contemplated. In this manner, a reliable connection between contact members 55 of adapter board 50 and contact members 40 of authentication board assembly 30 is consistently achieved, thus providing a robust communication link between chip 36 and handle assembly 12. In embodiments, contact assembly 38, contacts 40, and/or contacts 55 are formed at least in part from electrically conductive material, such as, without limitation, beryllium copper.

Figure 19:
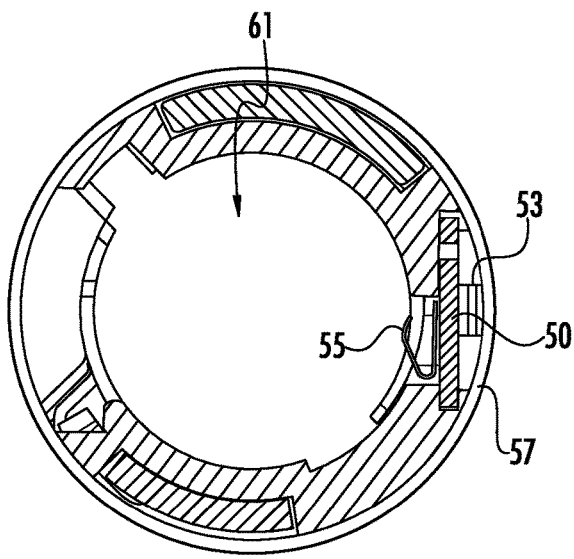
FIG. 19 is a cross-sectional, axial view of the adapter assembly shown in FIG. 3 showing the adapter assembly separated from the loading unit.
Figure 20:
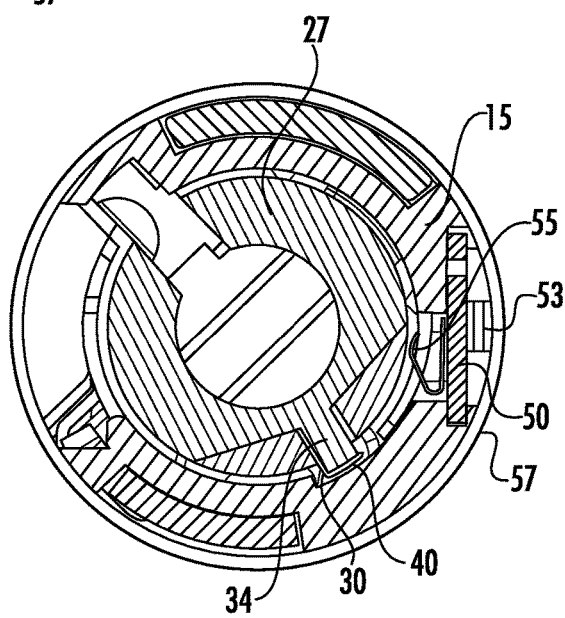
FIG. 20 is a cross-sectional, axial view of the adapter assembly shown in FIG. 3 showing the loading unit inserted into the adapter assembly.
Figure 21:
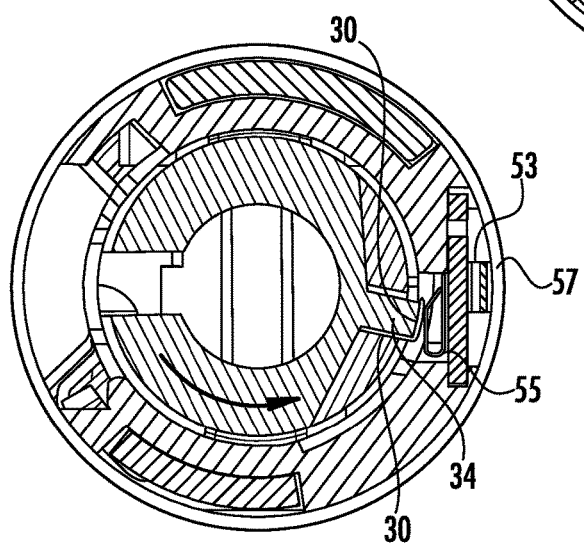
FIG. 21 is a cross-sectional, axial view of the adapter assembly shown in FIG. 3 showing the loading unit engaged with the adapter assembly.
Figure 22:
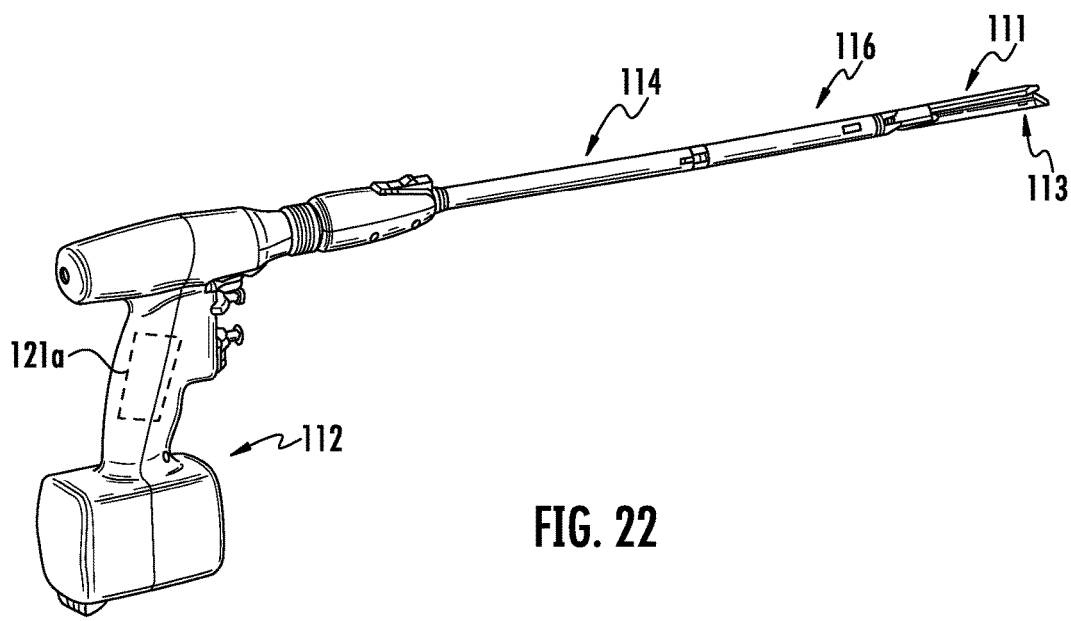
FIG. 22 is a perspective view of a surgical stapling device according to further embodiments of the present disclosure.
Figure 23:
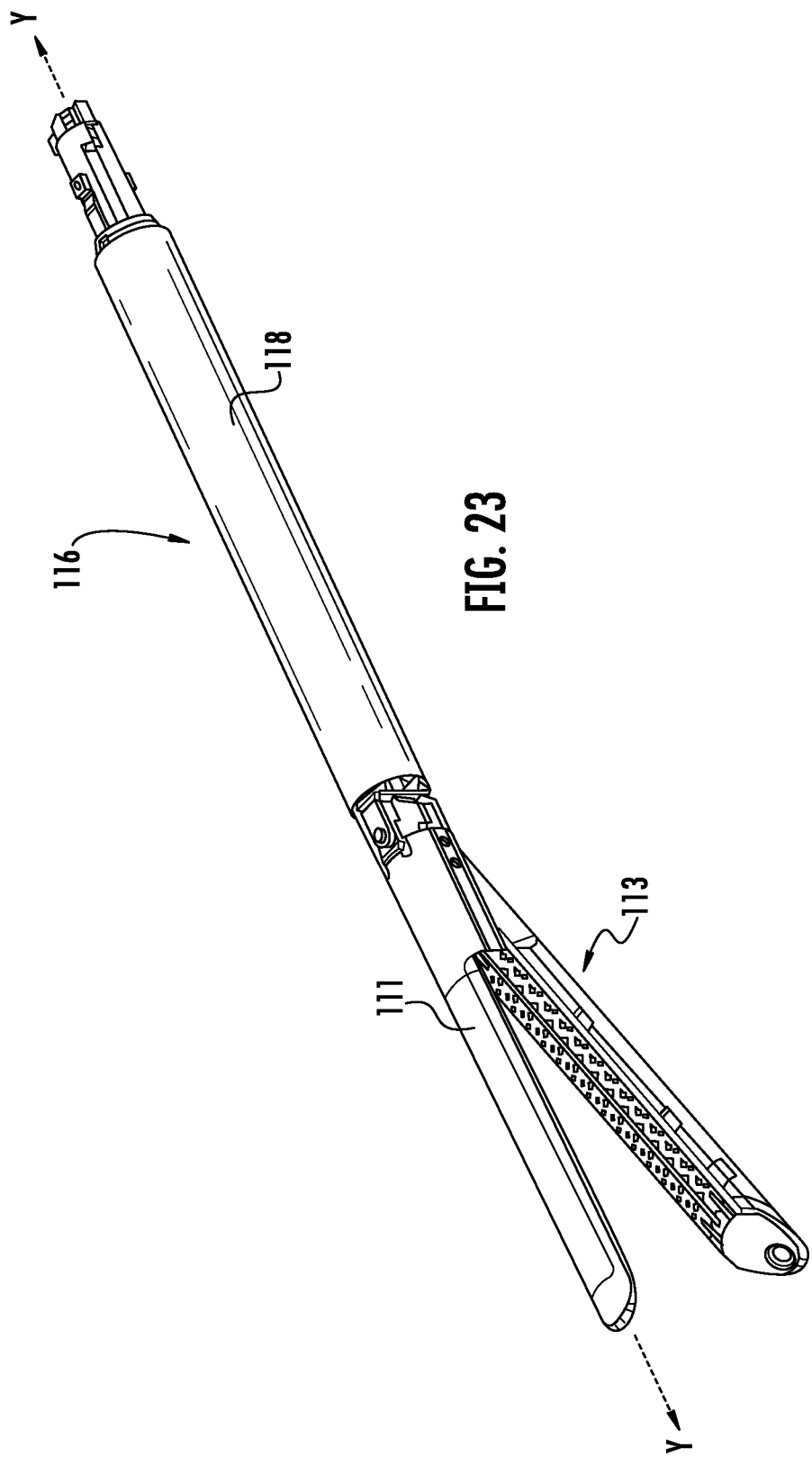
FIG. 23 is a perspective view of a loading unit according to embodiments of the present disclosure.
Figure 24:
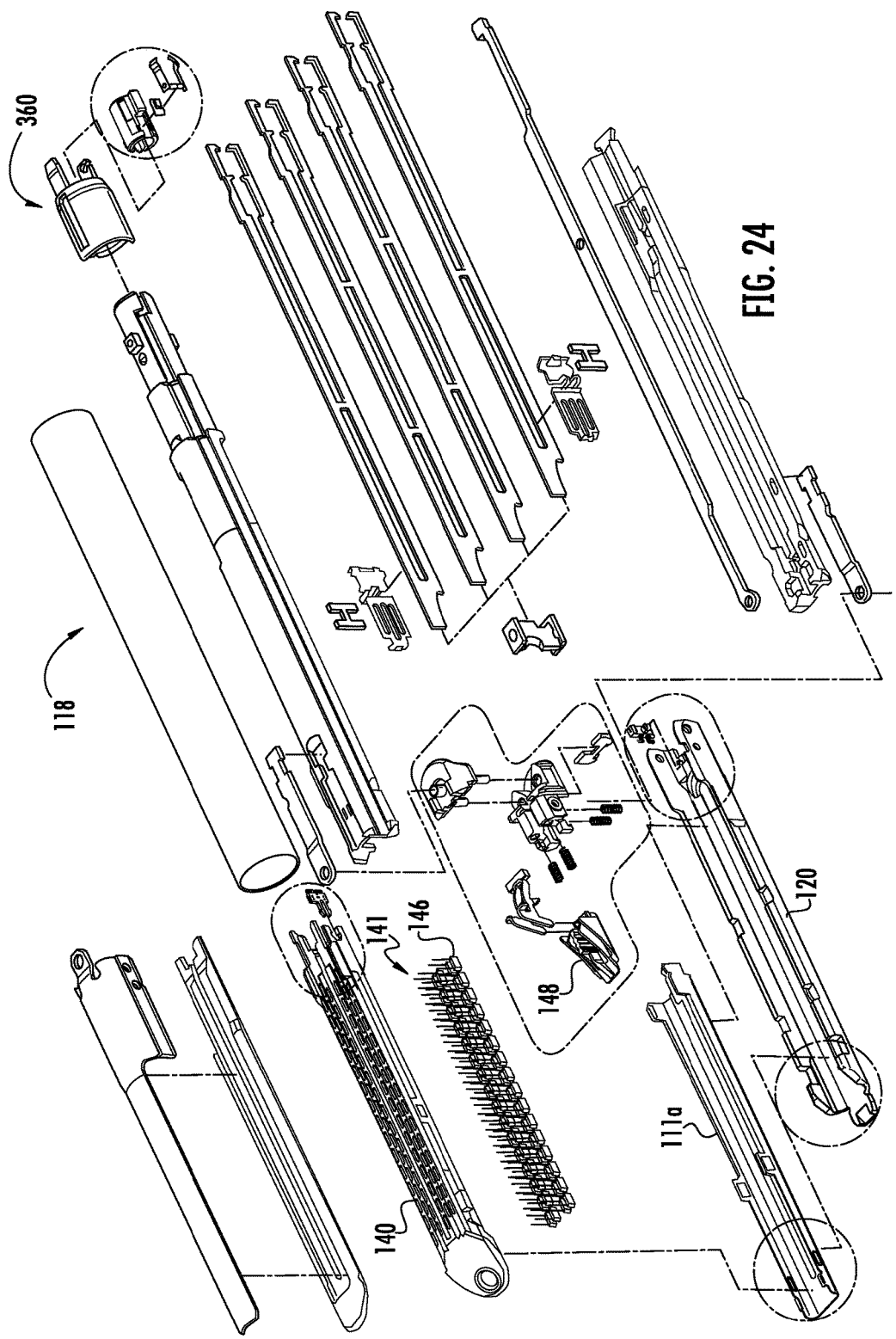
FIG. 24 is the loading unit of FIG. 23 shown with parts separated.
Figure 25:
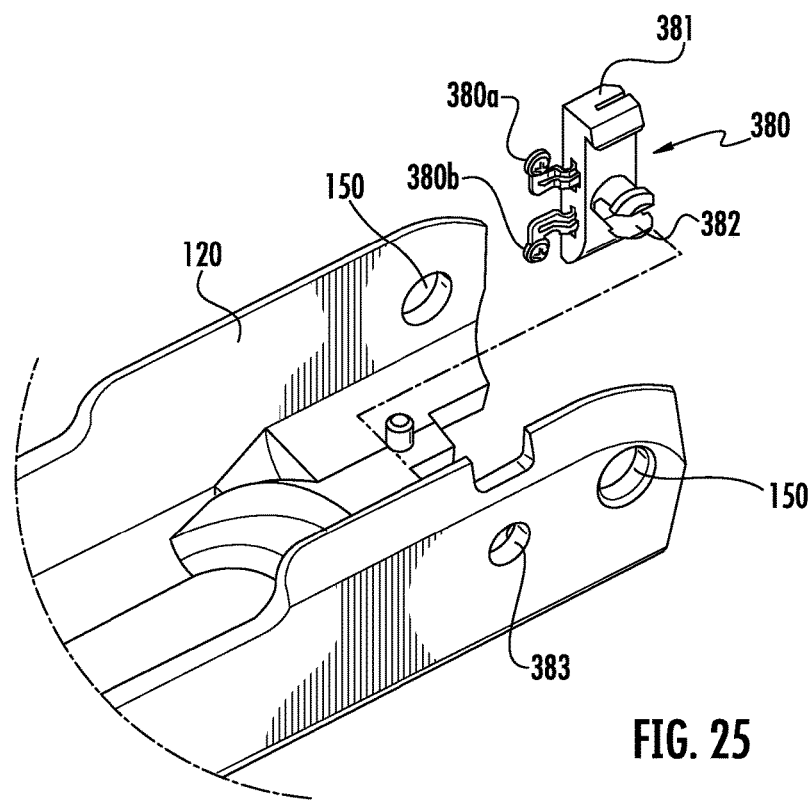
FIG. 25 is a detailed perspective view of a board assembly.
Figure 26:
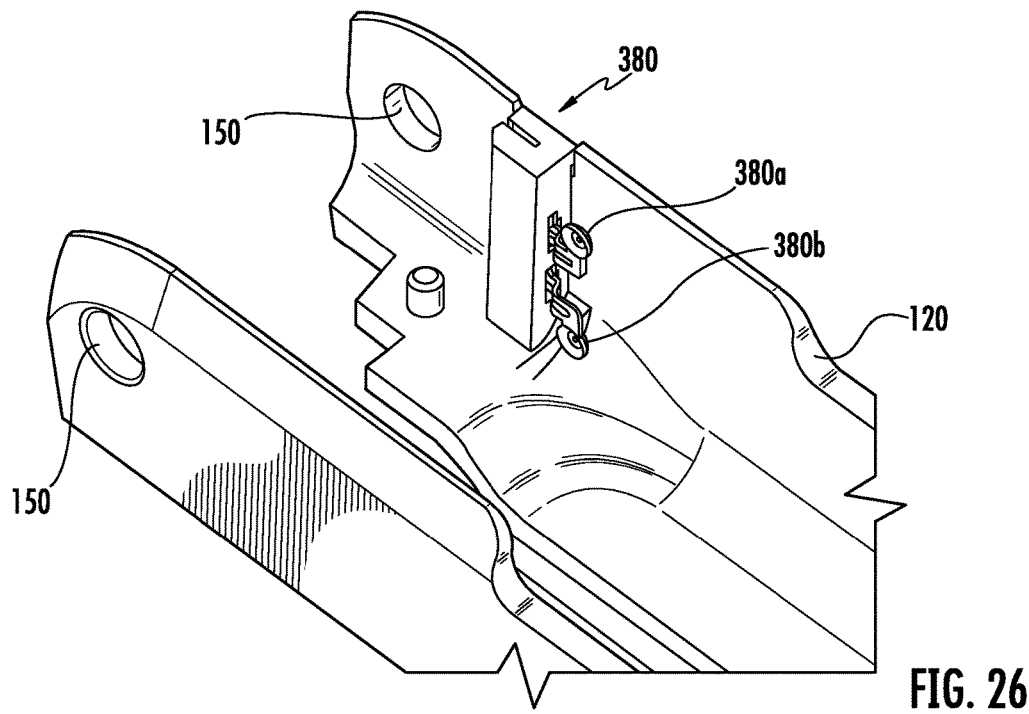
FIG. 26 is a another detailed perspective view of the board assembly of FIG. 25.

Turning now to FIGS. 15-21, the interaction between adapter board assembly 50 and authentication board assembly 30 is shown. As seen in FIGS. 15, 16, and 19, adapter board 50 is retained within loading unit adapter 15 by spring clip 52. Spring 53 bears against outer tube 57 to bias adapter board 50 inwardly towards bore 61, such that contact members 55 extend into bore 61. As adapter coupler 27 is inserted fully into bore 61 of loading unit adapter 15, the initial rotational orientation of adapter coupler 27 and loading unit coupler 15 is such that contact members 40 of authentication board 30 and contact members 55 of adapter board 50 are roughly 45° apart (FIG. 20). As loading unit 16 is rotated with respect to adapter assembly 14, contact members 40 of authentication board 30 are brought into engagement with contact members 55 of adapter board 50. Advantageously, contact support 34 of adapter coupler 27 of loading unit 16 provides radial support to contact members 30 as they engage mating contact members 55 of adapter board 50. In addition, spring 53 bears against outer tube 57 which enables adapter board 50 to float with respect to authentication board 30 and loading unit coupler 15, thereby compensating for manufacturing variations between the various components and providing a reliable connection between authentication board 30 and adapter board 50.

It is contemplated that a loading unit like loading unit 16 could have a removable and replaceable staple cartridge assembly. A stapling system is shown in FIGS. 22-57, in accordance with an embodiment of the present disclosure, having a powered handle assembly 112 similar to the handle assembly 12 discussed above. The handle assembly is configured as discussed above and has a controller 121a. The stapling system includes an adapter assembly 114 and a loading unit 116, each of which can be configured as discussed above. The loading unit is a linear stapling loading unit, but other types of loading units are contemplated. The loading unit 116 has a drive assembly for firing staples into tissue clamped between the anvil jaw member 111 and staple cartridge jaw member 113, as discussed above.

Supported in the staple cartridge jaw member 113 is a removable and replaceable staple cartridge assembly 115. A removable and replaceable staple cartridge assembly is disclosed in U.S. patent application Ser. No. 13/280,880, filed Oct. 25, 2011, and published as US 2013-0098965 A1, the entire disclosure of which is hereby incorporated by reference herein.

Loading unit 116 of the present disclosure is configured to be used more than once. In particular, the loading unit has the removable staple cartridge assembly 115 that includes the staple cartridge and drive assembly discussed above. The removable assembly 116 is configured to be removed and replaced (e.g., after firing staples or other surgical fasteners therefrom). The loading unit 116 shown includes a proximal body portion 118 that is attachable to the adapter assembly 114. However, the features of the loading units of the present disclosure can be incorporated in a surgical instrument in which does not include a detachable portion of the elongated portion of the instrument.

Loading unit 500 includes a proximal body portion 118 defining a longitudinal axis "A-A". Jaw members include an anvil jaw member 111 and a cartridge jaw member 113. One of the jaw members is pivotal in relation to the other to enable the clamping of tissue between the jaw members. In the illustrated embodiments, the cartridge jaw member 113 is pivotal in relation to the anvil jaw member and is movable between an open or unclamped position and a closed or approximated position. However, the anvil jaw member, or both the cartridge and anvil jaw member, can be movable. As discussed in connection with FIGS. 1-21, the anvil jaw member includes an anvil having a plurality of staple forming depressions.

The cartridge jaw member 113 includes a channel or carrier 120 which receives and supports the staple cartridge assembly 115. The cartridge assembly has a cartridge body 140 and a support plate 111. The cartridge body and support plate are attached to the channel or carrier 120 by a snap-fit connection, as discussed below, a detent, latch, or by another type of connection. The cartridge assembly includes fasteners or staples 141. Cartridge body 140 defines a plurality of laterally spaced staple retention slots 142, which are configured as openings (see FIG. 32). Each slot is configured to receive a fastener or staple therein. Cartridge assembly also defines a plurality of cam wedge slots which accommodate staple pushers 146 and which are open on the bottom to allow the actuation sled 148 to pass longitudinally therethrough in the firing of the staples as discussed above.

The removable staple cartridge assembly 115 includes cartridge body 140 and support plate 111. The removable assembly 115 is removable from channel 120, e.g., after staples have been fired from the cartridge body 140. Another removable and replaceable staple cartridge assembly is capable of being loaded into the channel, such that the loading unit 116 can be actuated again to fire additional fasteners or staples.

Channel 120 includes one or a pair of engagement structures 120a (such as slots) for engaging the staple cartridge assembly and support plate (see FIG. 39), a central slot for the passage of the drive beam, a pair of proximal holes 150 for connection with the anvil jaw member, and a ramped surface 152. Proximal holes 150 are configured to align with/mechanically engage a pair of corresponding holes or features on the anvil jaw member. The jaw members can be connected by pins, for example, to facilitate a pivotal relationship between anvil jaw member 111 and cartridge jaw member 113.

Figure 32:
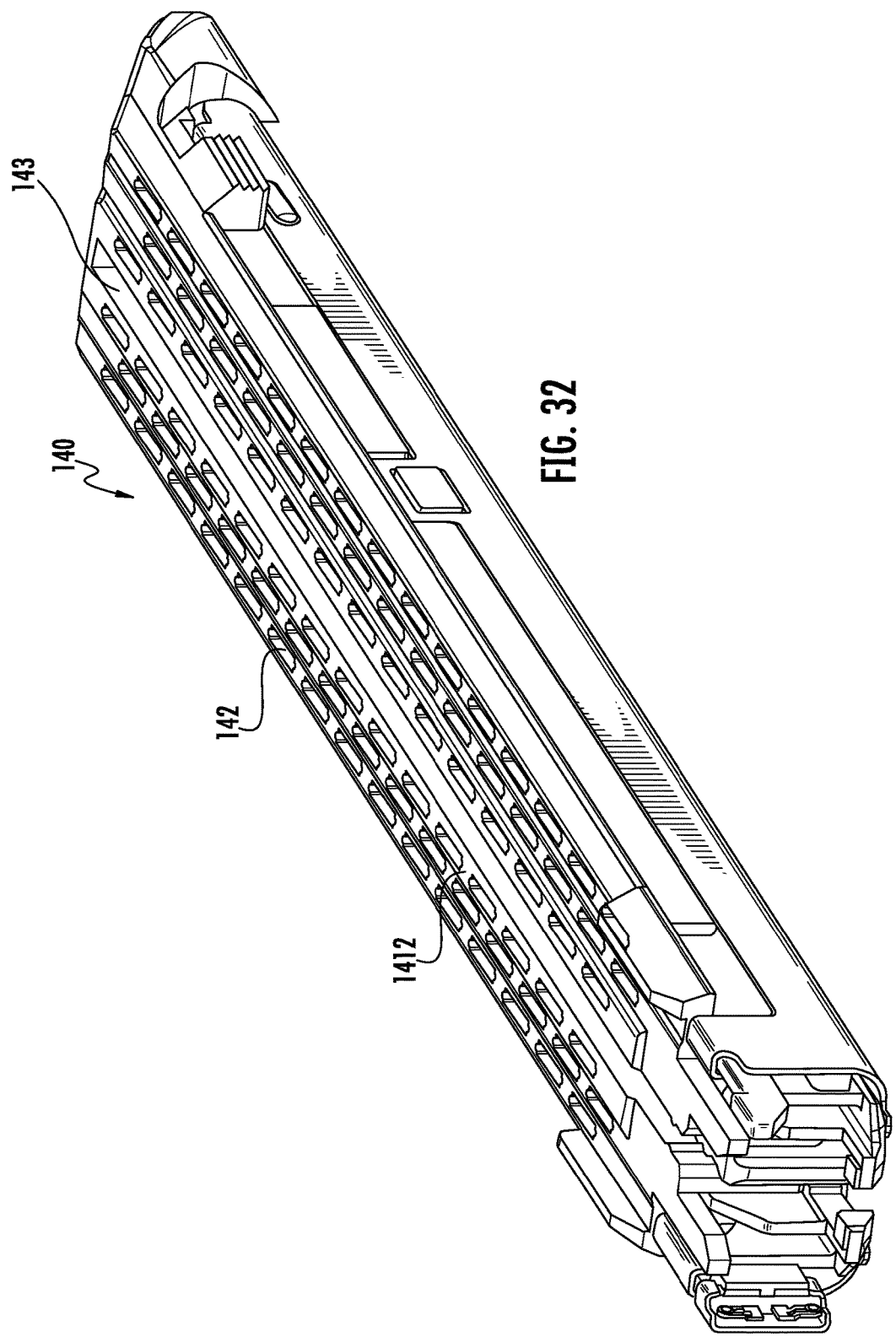
FIG. 32 is a top perspective view of a staple cartridge assembly in accordance with embodiments of the present disclosure.
Figure 38:
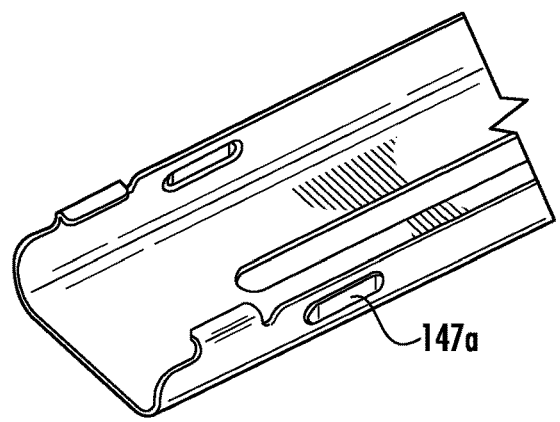
FIG. 38 is a perspective view of the proximal portion of a support plate of the staple cartridge assembly.
Figure 39:
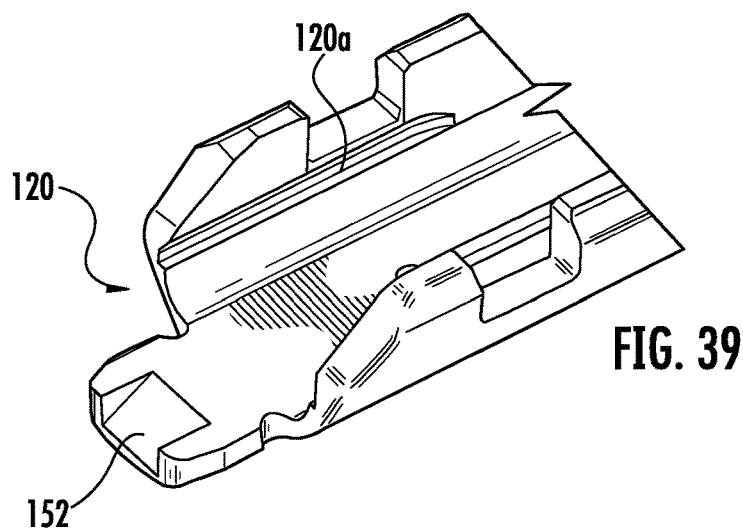
FIG. 39 is a perspective view of the proximal portion of a channel of the loading unit.
Figure 40:
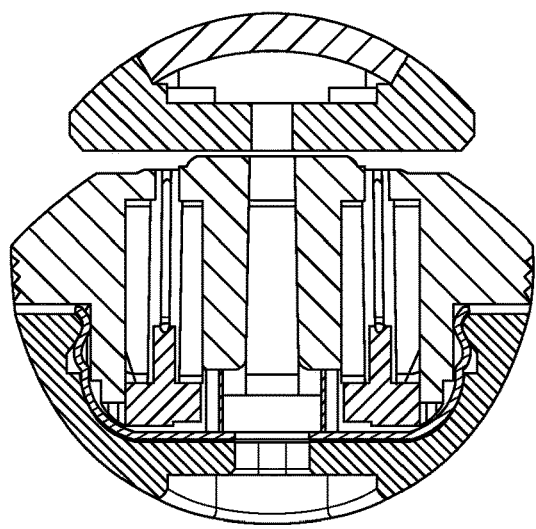
FIG. 40 is a cross sectional view of the loading unit.
Figure 41:
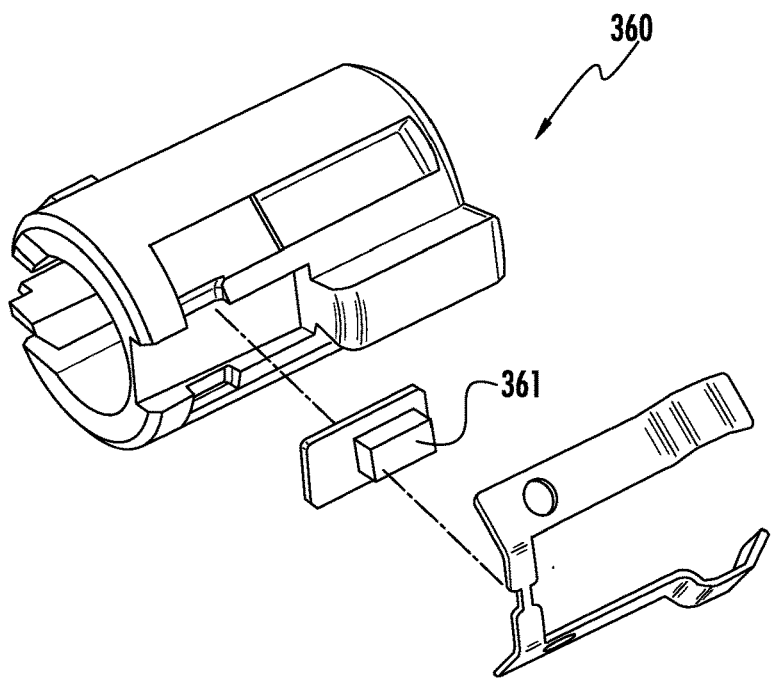
FIG. 41 is a perspective view of a chip assembly of the loading unit with parts separated.
Figure 42:
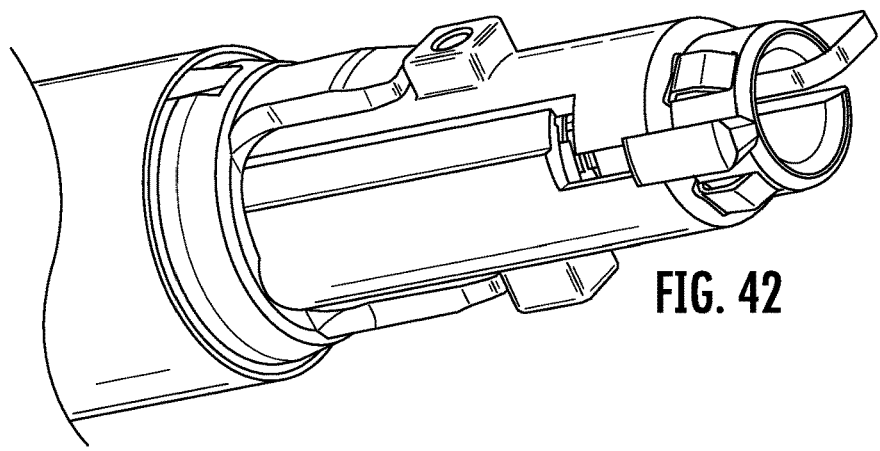
FIG. 42 is a perspective view of the proximal portion of the loading unit.
Figure 43:
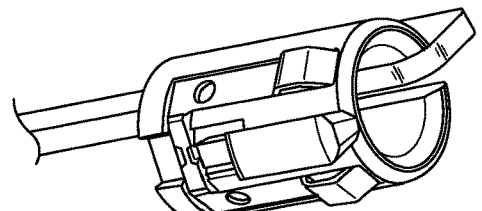
FIG. 43 is a perspective view of the chip assembly.
Figure 44:
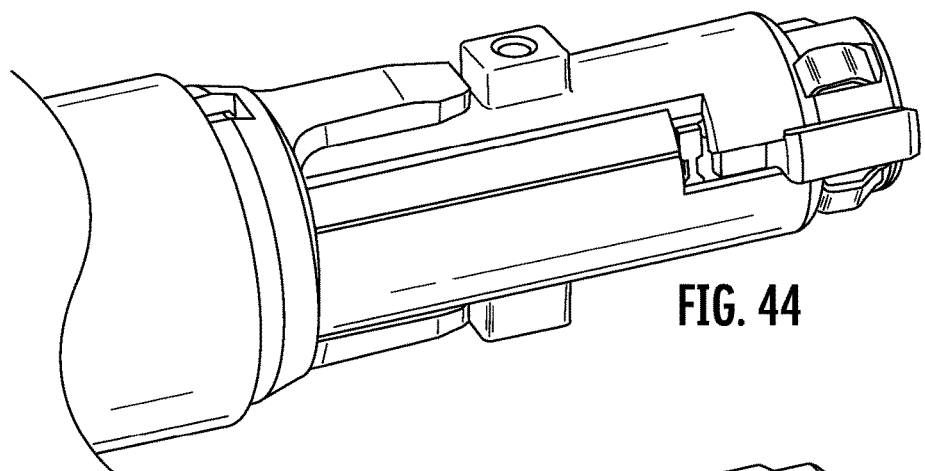
FIG. 44 is a perspective view of the proximal portion of the loading unit.
Figure 45:
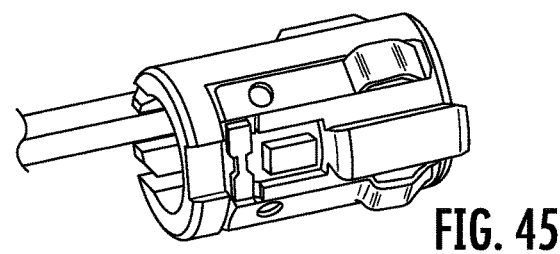
FIG. 45 is another perspective view of the chip assembly.
Figure 46:
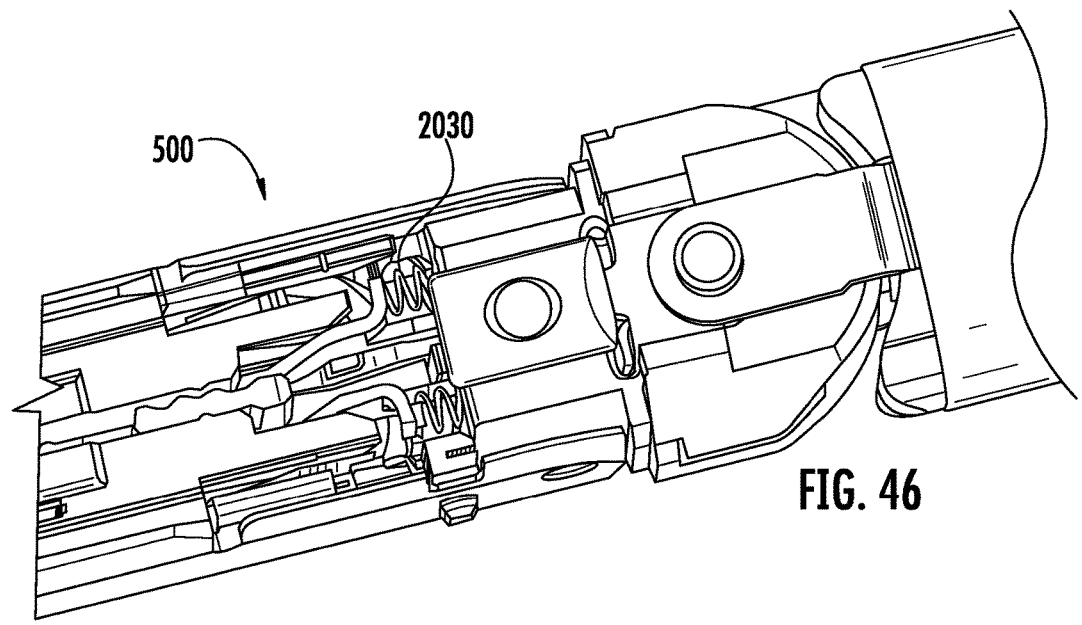
FIG. 46 is a detailed perspective view of a lockout assembly in accordance with embodiments of the present disclosure.
Figure 47:
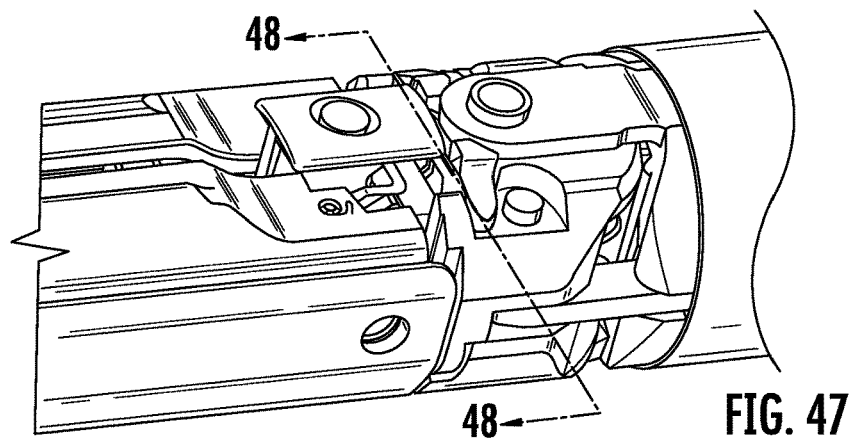
FIG. 47 is another detailed perspective view of a lockout mechanism in accordance with embodiments of the present disclosure.
Figure 48:
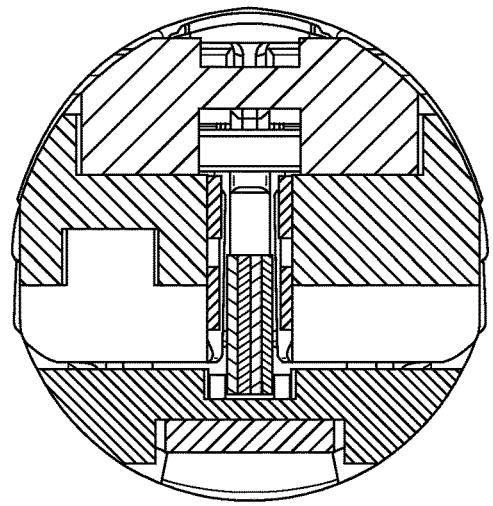
FIG. 48 is a cross sectional view through the drive beam.
Figure 49:
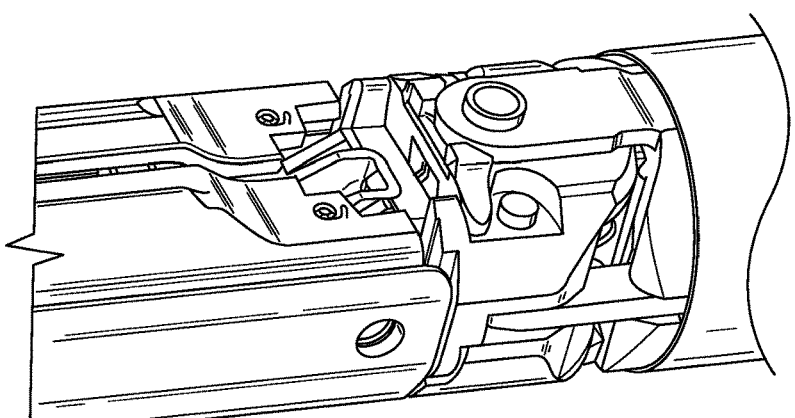
FIG. 49 is a another detailed perspective view of the lockout mechanism.
Figure 50:
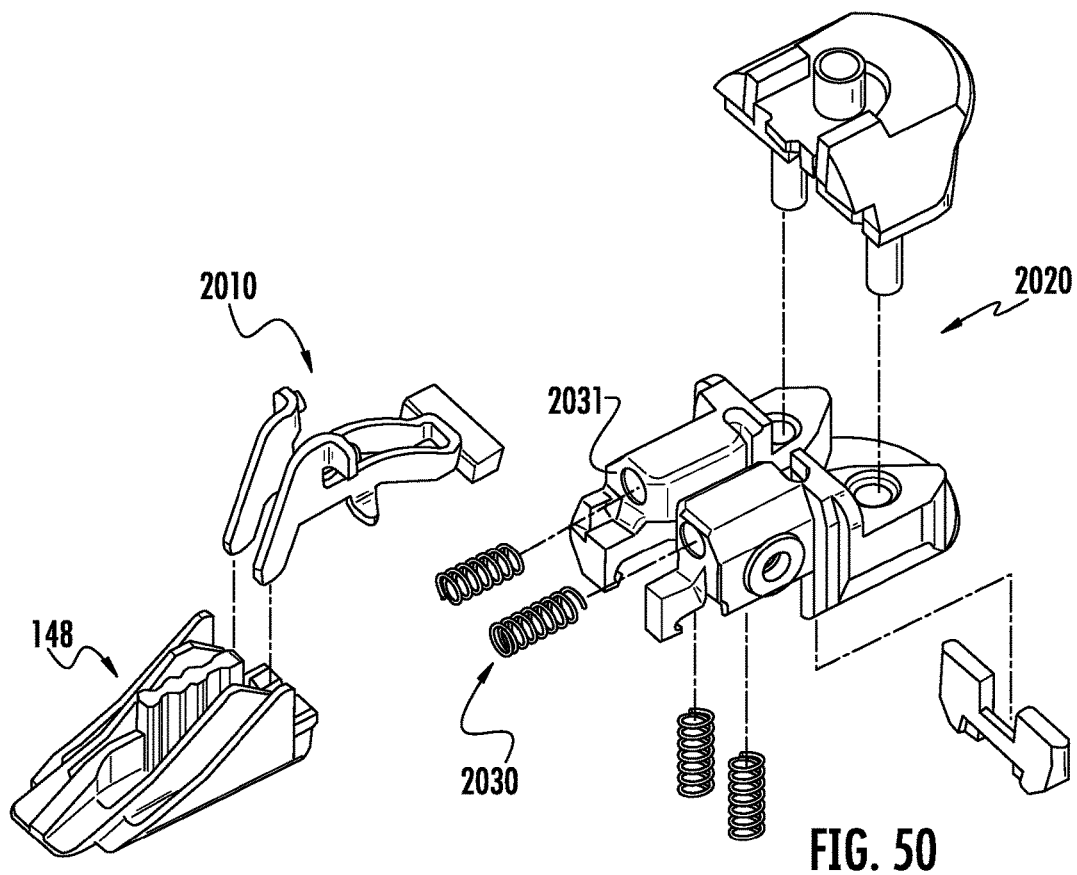
FIG. 50 is a perspective view with parts separated showing a latch, sled, and mounting portion.
Figure 51:
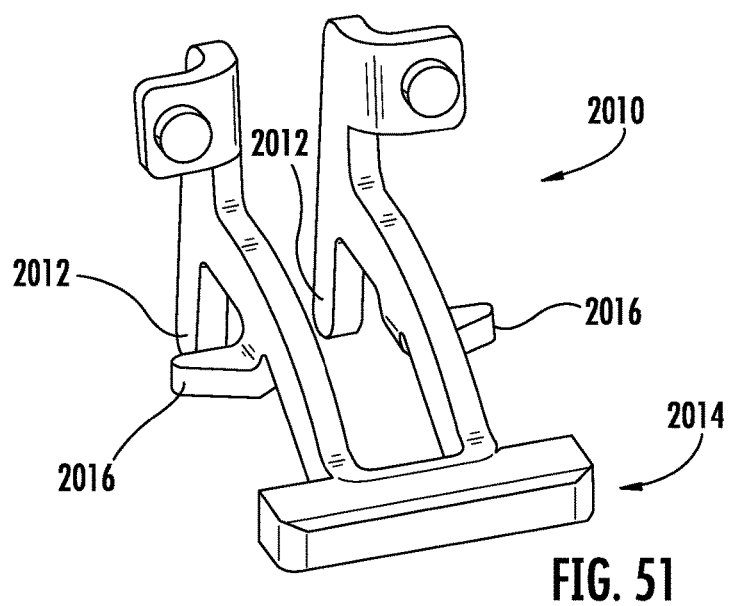
FIG. 51 is a perspective view of the latch.
Figure 52:
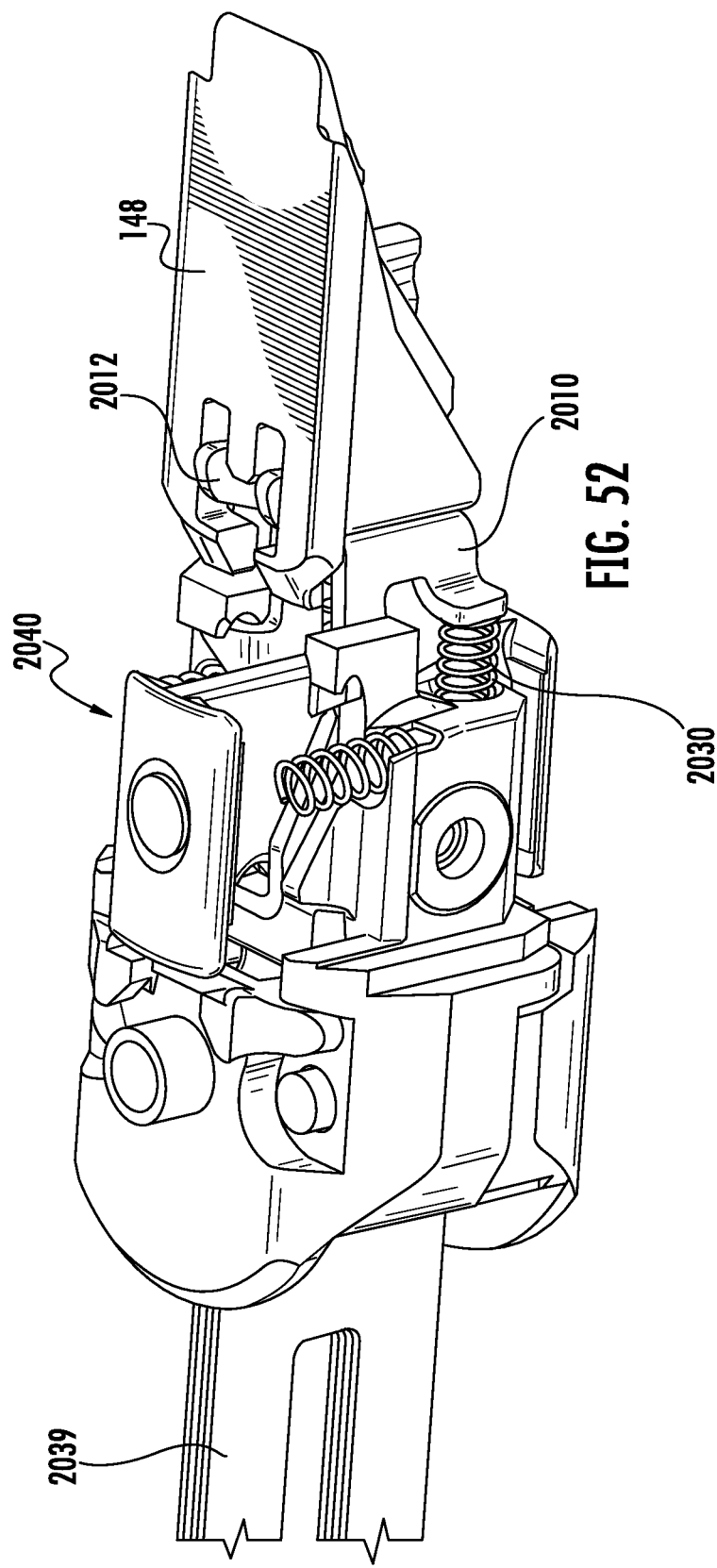
FIG. 52 is a perspective view of the loading unit with parts removed showing the lockout mechanism.
Figure 53:
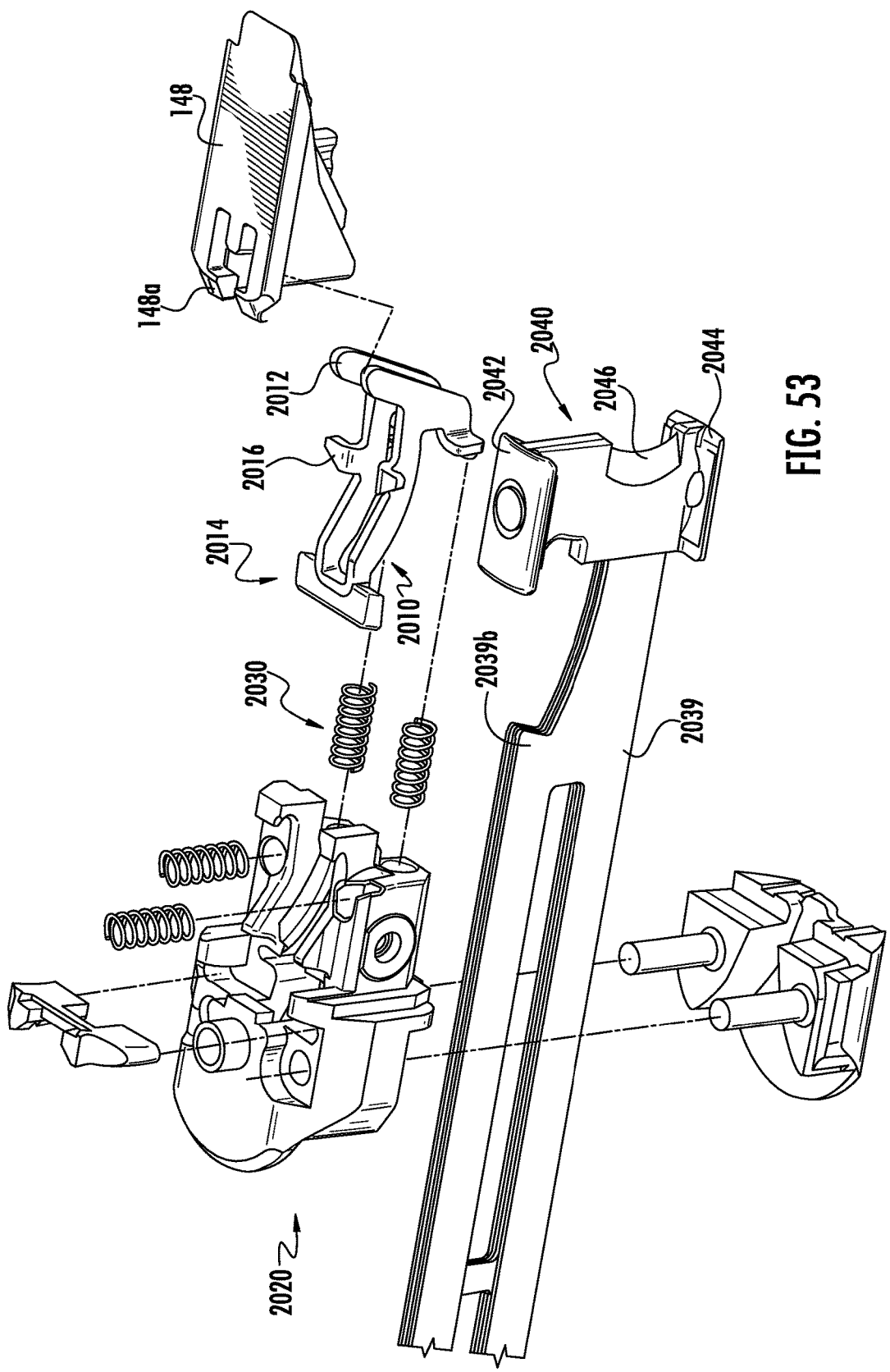
FIG. 53 is a perspective view of the lockout mechanism with parts separated showing the drive beam.
Figure 54:
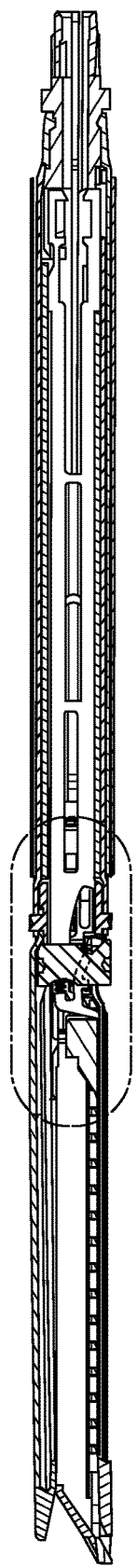
FIG. 54 is a cross sectional view taken longitudinally through the loading unit.
Figure 55:
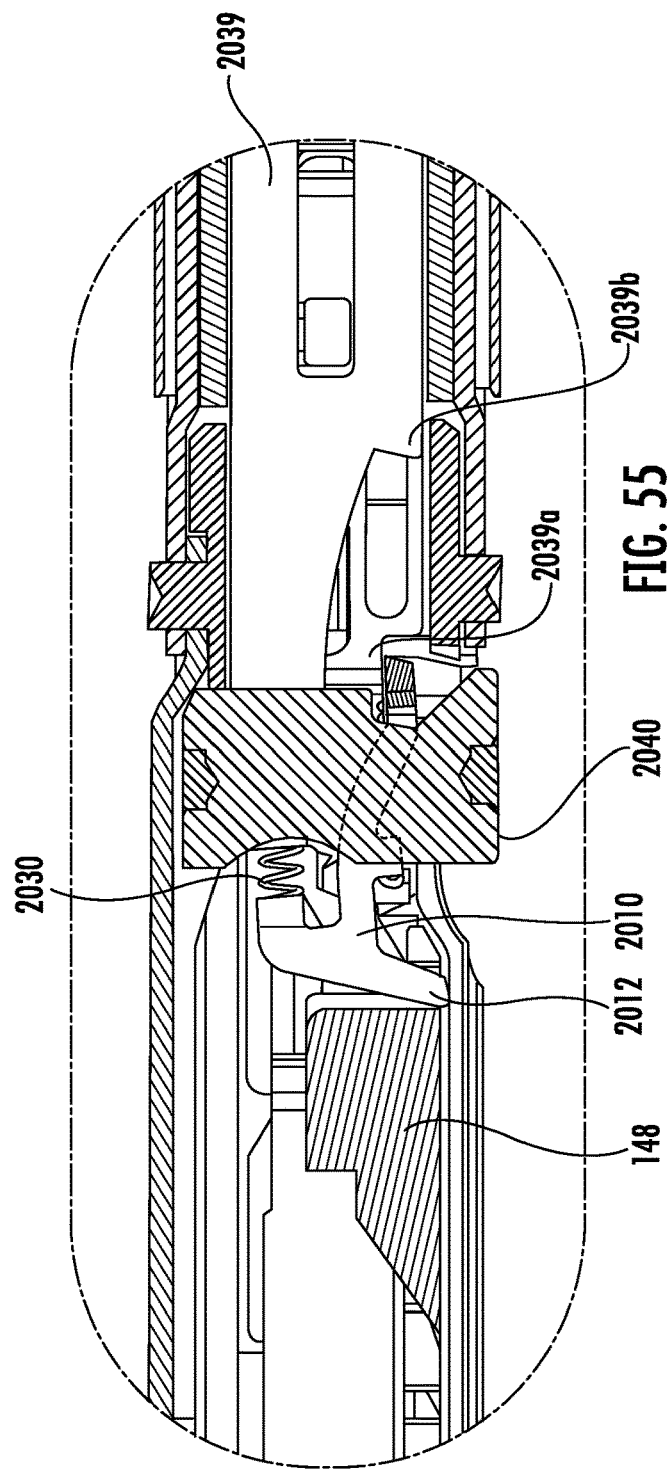
FIG. 55 is a detailed view of FIG. 54 showing the latch and dynamic clamping member.

The cartridge body 140 includes a central slot 143, and rows of staple retention slots positioned on each side of slot 143 (see FIG. 32). Cartridge body also includes a pair of engagement structures or protrusions which may, in certain embodiments, be slots or openings adjacent its proximal end for connection with the support plate 111a and/or channel 120.

Figure 29:
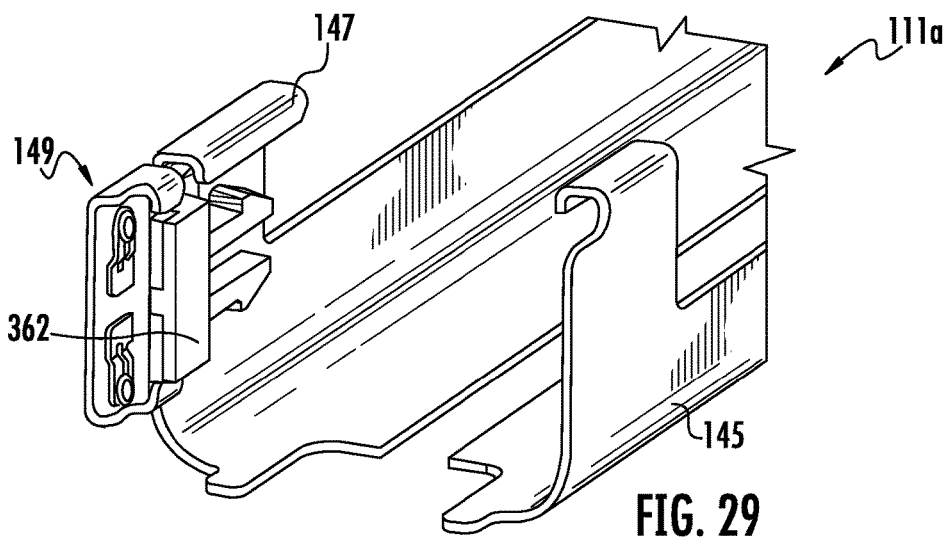
FIG. 29 is a detailed perspective view of a support plate in accordance with embodiments of the present disclosure.
Figure 30:
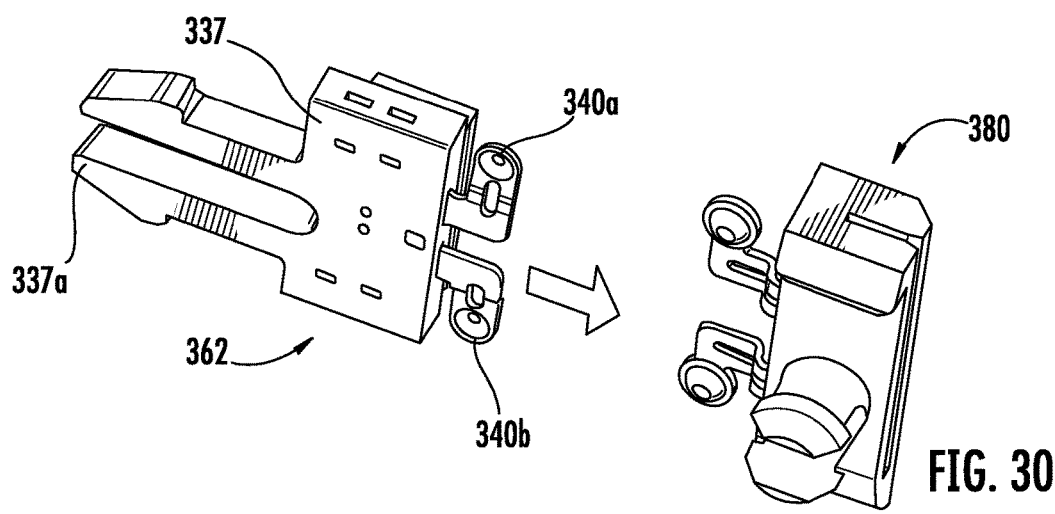
FIG. 30 is a perspective view of the chip assembly and board assembly of FIGS. 25-28.
Figure 31:
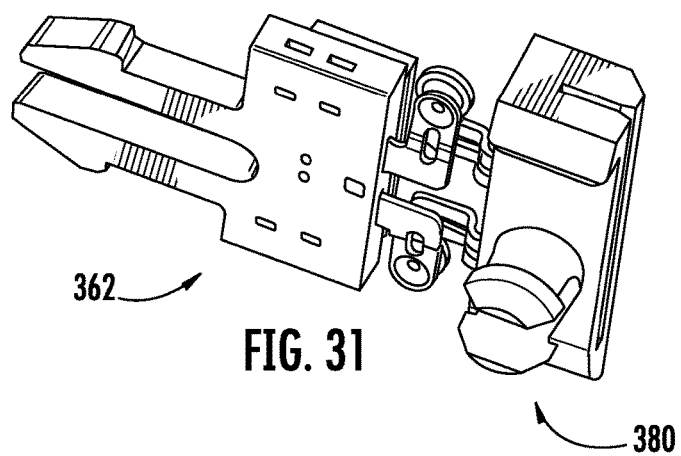
FIG. 31 is another perspective view of the chip assembly and board assembly of FIGS. 25-28.

With particular reference to FIG. 29, support plate 111a includes a base 145, engagement features 147 and 147a (see FIG. 38) for connection with the cartridge body and/or channel, and a mounting portion 149 at a proximal end thereof (see FIG. 29). The support plate 111a is disposed underneath the cartridge body to support the staple pushers, actuation sled, and staples (or other surgical fasteners) and prevent those components from falling out of the staple cartridge assembly.

The loading unit can include a chip assembly 360 mounted on a proximal end of the proximal body portion 118, as shown in FIGS. 41-45, for example. The chip assembly is as described above in connection with the authentication board assembly 30 discussed above. The chip assembly 360 is mounted for connection with a board assembly in a coupler on the distal end of the adapter assembly 114, and can be configured as discussed above in connection with FIGS. 1-21. The chip assembly 360 includes a chip 361 for authentication and information purposes, and can include a memory that stores certain information. The information can include the type of device the loading unit is, the version of the device/loading unit, the name of the loading unit, the manufacturing lot number, the serial or other identification number, the maximum force to which the drive beam of the loading unit can be driven, the interlock zone (mm), the end zone (mm), whether or not the loading unit can articulate, and/or a usage limit (the number of times the loading unit can be used). The interlock zone is the position of the drive beam, in millimeters, measured from the start or initial position of the drive beam, when the drive beam is engaged by a lockout in the loading unit. An example of a lockout is discussed below. The end zone is the position of the drive beam, in millimeters, measured from the start or initial position of the drive beam, when the drive beam has reached the end of its travel in the staple cartridge body 140. Since the staple cartridge assembly 115 can be removed and replaced, there is an intended limit to the number of times the loading unit can be reloaded with a fresh unfired staple cartridge. The information stored on the chip can include the staple line length and/or length of the staple cartridge.

The controller 121a in the handle assembly 112 can be programmed to read the information on the chip 361 or receive instructions from other controllers as a function of information stored in chip 361. This information is used in the operation of the surgical system. Desirably, some or all of the information is encrypted, which can be accomplished as discussed above in connection with FIGS. 1-21. The controller can be programmed to not provide power to a motor (not shown) disposed in the handle assembly 112, and not operate the adapter assembly and loading unit, in the event that the serial number or other data is not recognized. Varying levels of function can be enabled or disabled based on the authentication status of any system chip (including but not limited to chip 361). For example, a system which does not successfully authenticate may be set to allow the stapling reload to clamp, articulate, and rotate at a reduce speed, but not fire. The maximum force information is used in conjunction with a load sensor, such as a strain gauge, disposed in the surgical system. For example, a load sensor can be disposed in the adapter assembly 114 and/or loading unit, such as a load sensor on the drive beam. The controller is programmed to compare the data from the load sensor to the maximum force data stored on the chip so that, for example, the operation of the motor (not shown) is interrupted or altered before the maximum force is exceeded. In another example, the controller can be programmed to operate in "slow mode" if the measured force reaches a predetermined level or when any other triggering metric is satisfied. The predetermined level of force can be the maximum force discussed above, or another level of force, stored on a chip in the system, such as chip 361. Slow mode means that the controller operates the motor (not shown) at a slower rate, and also delaying the compression of tissue and/or firing of staples. In thick tissue, slow mode can allow fluid in the tissue to move away from the site of stapling, facilitating more compression of the tissue. Alternative methods of load detection can be used, such as sensing changes in tissue thickness, rate of change in thickness or compression, monitoring the current draw in the motor of the handle assembly, the velocity of the movement of the drive assembly, etc.

It is contemplated that the controller can have a feedback loop that is used to determine how the motor in the handle assembly should be operated. The controller can be programmed to compare a profile of force over time, or load over time. The operation of the motor (not shown) is interrupted or altered if the pattern of force or load is not as would be expected for the particular loading unit, or before some predetermined maximum or other limit is reached. The controller can also be programmed to operate in "slow mode" as discussed above, based on the profile.

In a similar manner, the operation of the motor can be stopped or operated in slow mode if the drive beam is disposed in the interlock zone, end zone, or other areas of specific interest. Furthermore, the controller can interrupt or prevent the operation of the articulation linkage, bar or cable if the data on chip 361 indicated that the loading unit does not articulate. Similarly, the controller can interrupt or alter the characteristics of system rotation if the data on chip 361 indicated that the loading unit is of a specific type.

It is contemplated that the chip 361 with some or all of the data discussed above can be provided in any of the embodiments disclosed herein, including loading units that do not have a removable and replaceable staple cartridge assembly, and/or loading units that do not articulate.

It is contemplated that the information on chip 361 can be read by the controller in the handle assembly, another chip in the system, or any other computer component in the surgical system.

In any of the embodiments disclosed herein, the controller can write information to the chip on the loading unit. For example, the maximum force that was used to clamp onto tissue, as measured by the load sensor discussed above, the maximum force that was used to fire staples, and/or the position of the drive beam when the drive beam stops advancing, etc. Other information that can be written to the chip 361 includes the location of the drive beam when the device entered into slow mode, the number of times the loading unit has been fired, whether the loading unit has been fired, the type of handle assembly, the serial number of the handle assembly, the type of adapter assembly, the date and time of key events, the orientation of components of the surgical system, temperature, and/or the serial number of the adapter assembly. The maximum force to fire staples can be saved along with the position of the drive beam, in any of the embodiments disclosed herein. The information can also be saved in memory connected to the controller in the handle assembly, other chip(s) in the system, or other computer components of the surgical system.

It is also envisioned, in any of the embodiments disclosed herein, that an end effector or tool assembly is arranged for articulating between a first position where tool assembly is aligned with longitudinal axis "Y-Y," and a second position where tool assembly is disposed at an angle with respect to longitudinal axis "Y-Y." For example, the tool assembly, which includes the anvil jaw member and the cartridge jaw member, may be mounted so as to be pivotable with respect to the proximal body portion 118. The anvil jaw member and cartridge jaw member can be attached to a mounting assembly 2020 (discussed further below), and the mounting assembly can be pivotably connected to the proximal body portion 118. The loading unit 116 includes one or more cables or linkages disposed in the proximal body portion so that when the cable or linkage is displaced, the tool assembly pivots and articulates with respect to the instrument. Further details of providing articulation are described in detail in commonly-owned U.S. Pat. No. 6,953,139 to Milliman et al., the contents of which are hereby incorporated by reference in their entirety. The adapter assembly 114 can include a linkage, bar or cable for enabling the articulation of the tool assembly.

As seen in FIG. 32, for example, any of the embodiments disclosed herein can include a cartridge body 140 having a stepped tissue-contacting surface 1412. In such embodiments, different sized staples, or all the same sized staples, may be used. Further details of a staple cartridge having multiple staple sizes are included in U.S. Pat. No. 7,407,075 to Holsten et al., the entire contents of which are hereby incorporated by reference herein. The staple forming recesses of the anvil, or the staple pushers, or both, can be configured accordingly, to form the staples in the desired shape and size.

Figure 27:
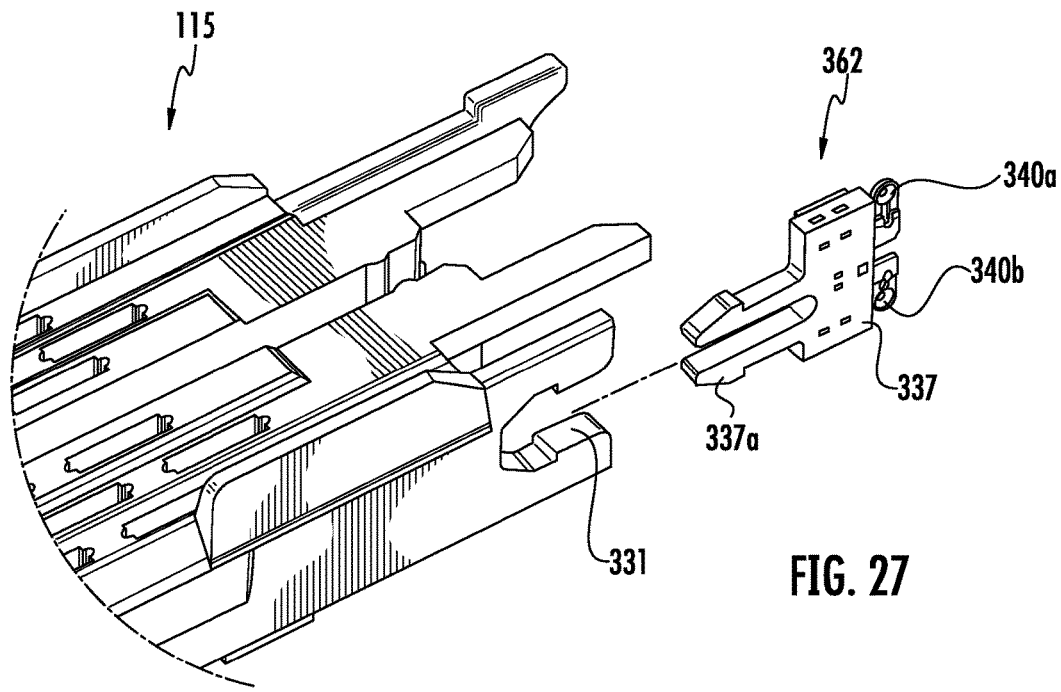
FIG. 27 is a detailed perspective view of a chip assembly.
Figure 28:
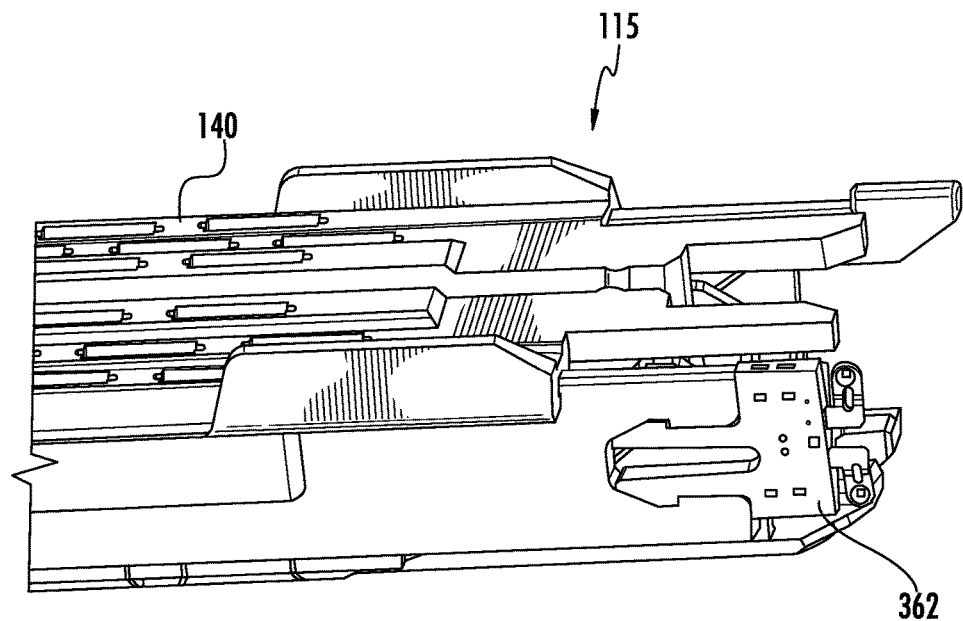
FIG. 28 is another detailed perspective view of the chip assembly of FIG. 27.

The removable and replaceable staple cartridge assembly 115 can further include a chip assembly 362. (see FIGS. 27 and 28). A corresponding board assembly 380 (FIGS. 25 and 26) is disposed on the tool assembly of the loading unit 116, and may be disposed on the channel 120. The tool assembly board assembly 380 can be configured as discussed above in connection with the adapter board assembly 50 of the adapter coupler 27. The tool assembly board assembly 380 is configured to be securely mounted on a wall of the channel 120. This board assembly 380 is positioned such that when cartridge assembly 140 is secured to the channel 120 of the loading unit, the chip assembly 362 engages the board assembly 380 mounted on the channel. (See FIGS. 29-31). FIGS. 27 and 28 show the relationship between the chip assembly and the staple cartridge body 140, whereas FIG. 29 shows the relationship between the chip assembly 362 and the support plate 111a.

In more detail, chip assembly includes a body 337 and a pair of contact members 340a, 340b (collectively, contact members 340) connected to a chip 336 disposed in the body. Body 337 defines a rectangular member having flexible arms with snap features 337a thereon. The flexible arms are configured to be securely received within a recess 331 defined by in the cartridge body. Chip 336 is in electrical communication with contact members 340.

Chip 336 includes any chip capable of storing information concerning the staple cartridge assembly 115. The chip can be the same as or similar to the chip of authentication board assembly 30. In any of the embodiments disclosed herein, any of the chips can store information such as, without limitation, cartridge size, staple arrangement, staple line length (or cartridge length), date of manufacture, expiration date, compatibility characteristics, a unique identifier (e.g., a serial number), and/or number of uses, as well as whether or not the staple cartridge assembly has been used. Such information can be transmitted to the controller in the handle assembly 112, or to another computer component through an appropriate bus, pin connection, wireless means, etc. In some embodiments, chip 336 includes an erasable programmable read only memory ("EPROM") chip. The controller in the handle assembly can write information to the chip 336. In this manner, the handle assembly 112 may adjust the firing forces, firing stroke, and/or other operational characteristics thereof in accordance with the information concerning the staple cartridge assembly that are transmitted from chip 336. The handle assembly 112 can communicate to chip 336 that the staple cartridge assembly has been used, which can prevent reloading or reuse of an expended reload assembly, or any other unauthorized use. The information stored in any of the components in the surgical system can be encrypted or obscured using private key encryption, public key encryption, and/or secure hash algorithms.

In any of the embodiments disclosed herein, the information stored on a chip of a component in the surgical system can include the type of component, the reorder code, the serial number, the identification code, the lot number, the compatibility with the system, the expiration date, the manufacture date, the date of programming, the design version, the bill of materials, surgeon preferences, performance characteristics, and/or the branding for the component. For example, such information can be stored on chip 361 or chip 336. It is contemplated that specialized or customized loading units may be produced, based on surgeon preference, and/or loading units that are operated in a "slow mode" or "fast mode", based on information stored in a chip or chips in the loading unit, staple cartridge assembly, etc.

In any of the embodiments disclosed herein, a removable and replaceable staple cartridge assembly, the loading unit, and/or the controller can include a chip or memory storing information concerning articulation of the tool assembly. The surgical system includes certain sensors and/or encoders, such as Hall effect sensors, radial encoders, linear encoders, potentiometers, accelerometers, force transducers, etc., that can determine the position of the drive assembly in the loading unit, and/or corresponding components in the adapter assembly. For example, the tool assembly includes an articulation linkage that actuates the articulation of the tool assembly. The controller can monitor the position of the linkage via the sensors or encoders, and determine the extent to which the tool assembly has been articulated. Furthermore, the number of times the tool assembly was articulated can be stored in a chip or memory of the staple cartridge assembly, adapter, controller, or other computer component. Information about the position of the linkage when the tool assembly has reached a fully articulated position can be stored.

The board assembly 380 (see FIGS. 25 and 26) also has a pair of contacts 380a and 380b and a body 381. The board assembly is mounted for contact with the chip assembly 362 when the staple cartridge assembly is properly mounted in the channel 120. The contacts 380a, 380b, 340a, and 340b have an L-shaped configuration as seen in the figures so that they may resiliently engage one another. The body 381 can define a snap feature 382 that is provided to engage a hole 383 in the channel to securely mount the board assembly.

The board assembly is appropriately connected to a bus, wires, or has a wireless communicator for transmittal of the information from chip assembly 362 to the controller in the handle assembly, and from the controller to the chip assembly, or to and from any other computer device.

In any of the embodiments disclosed herein, a lockout mechanism 500 is disposed in the loading unit. The loading unit may be configured as discussed above. Furthermore, the present disclosure is directed to a removable assembly having the lockout, or a loading unit having the lockout.

The lockout mechanism 500 includes a latch 2010 and at least one spring 2030, and is configured to prevent re-firing of a staple cartridge assembly 115 or staple cartridge 26, and also prevent distal translation of a drive beam after the staple cartridge has been fired and prior to loading of another cartridge assembly 115. The lockout mechanism 500 is shown alongside the sled 148 and mounting assembly 2020 in FIG. 50. The at least one spring 2030 is mounted on a distally facing surface 2031. For example, recesses are formed in surface 2031 for receiving springs 2030. Corresponding posts are provided on a proximally facing surface of the latch 2010. The latch is configured to be pivotable within the loading unit, and includes at least one prong 2012, a rear portion 2014, and a supporting portion 2016. The latch is configured to pivot around the supporting portion 2016, shown in FIGS. 50 and 51 as two downwardly depending features, and is biased by the spring or springs 2030. The sled 148 has a hole or recess for receiving the at least one prong 2012 when the latch and drive beam are in their initial positions. (see FIG. 52). The drive beam 2039 can interact with, or include, a dynamic clamping member 2040 having an upper flange 2042, lower flange 2044, and knife blade 2046. (see FIG. 53).

In the initial position, the latch 2010 is biased in a forward or distal direction, with the rear portion 2014 in contact with an edge 2039a on the drive beam 2039, preventing further rotational movement of the latch. As the drive beam and dynamic clamping member are moved in a forward or distal direction, the dynamic clamping member pushes the sled distally. A rear portion 148a of the sled pushes the prong or prongs 2012, tilting the latch against the bias of the at least one spring 2030. This removes the rear portion 2014 from the area near the edge 2039a, and allows the drive beam and dynamic clamping member to move forward. After the dynamic clamping member passes the latch 2010, the latch rotates forwardly under the influence of the spring. (see FIG. 57).

After the dynamic clamping member and sled have fired the staples from the cartridge 140, the dynamic clamping member is moved proximally, leaving the sled at the distal end of the cartridge 140 and cartridge assembly 115. The dynamic clamping member can move past the latch 2010, as cam surface 2041 moves the latch out of the path of travel (see FIG. 57). Once the dynamic clamping member returns to the initial position, the latch 2010 will prevent another forward movement of the dynamic clamping member 2040. The latch rear portion 2014 is in a position to engage another edge 2039b of the drive beam. (see FIG. 57). If the loading unit is of the type that accepts removable and replaceable staple cartridge assemblies 115, the cartridge assembly 115 can be configured to return the latch 2010 to the initial position, so that the drive beam and dynamic clamping member can again be moved distally to fire another set of staples.

As discussed above, any of the embodiments disclosed herein can include a chip assembly 360 on a surgical stapling loading unit, like loading unit 116, that has information on it concerning the lockout mechanism, such as the lockout mechanism discussed above. Furthermore, information can be stored on the chip 361 concerning the lockout mechanism. For example, the fact that the lockout mechanism was engaged can be recorded in chip assembly 360 and/or chip assembly 362 by the controller in the handle. The controller in the handle can include a memory for storing information, including a processor, and other computer components. The controller can also include a current meter, or ammeter, to measure the current in the motor of the handle assembly. The controller can be programmed to record the peak current reached during use of the loading unit and/or staple cartridge assembly, and can record that peak current on any of the chips or other computer components in the system. A peak current reached after the staples have been fired can be an indication that the loading unit was attempted to be fired a second time before a fresh staple cartridge assembly was mounted in the loading unit. Alternatively, the lockout mechanism can include a sensor such as, for example, on the latch. It is contemplated that the surgical system can include loading units that do not have a lockout mechanism like the one discussed above. The fact that the loading unit does not have a lockout mechanism can be stored in chip 361.

One of the types of encoders that can be included is one in the handle assembly. An encoder can be provided that determines how many rotations of the motor output shaft, or any other part of the system, have been made, and that can be used to determine a position of drive bars, linkages, cables, etc., in the adapter assembly, the firing bar in the loading unit, or other components. Alternatively, other sensors can be used to determine the position of various components in the surgical system.

The adapter assembly disclosed herein, in any of the embodiments disclosed herein, can be configured as disclosed in U.S. Published Application No. 2011/0174099 A1, the entire disclosure of which is hereby incorporated by reference herein. The motor in the handle assembly provides a rotational output on a rotating shaft and the adapter is configured to transform that output to a linearly moving linkage or bar, and can also provide drive to an articulation linkage in the proximal body portion 118 of the loading unit 116. The handle assembly and/or adapter assembly can be configured as disclosed in U.S. Published Application Nos. 2014/0012289 A1 and 2014/0110453 A1, the entire disclosures of which are hereby incorporated by reference herein.

Figure 58:
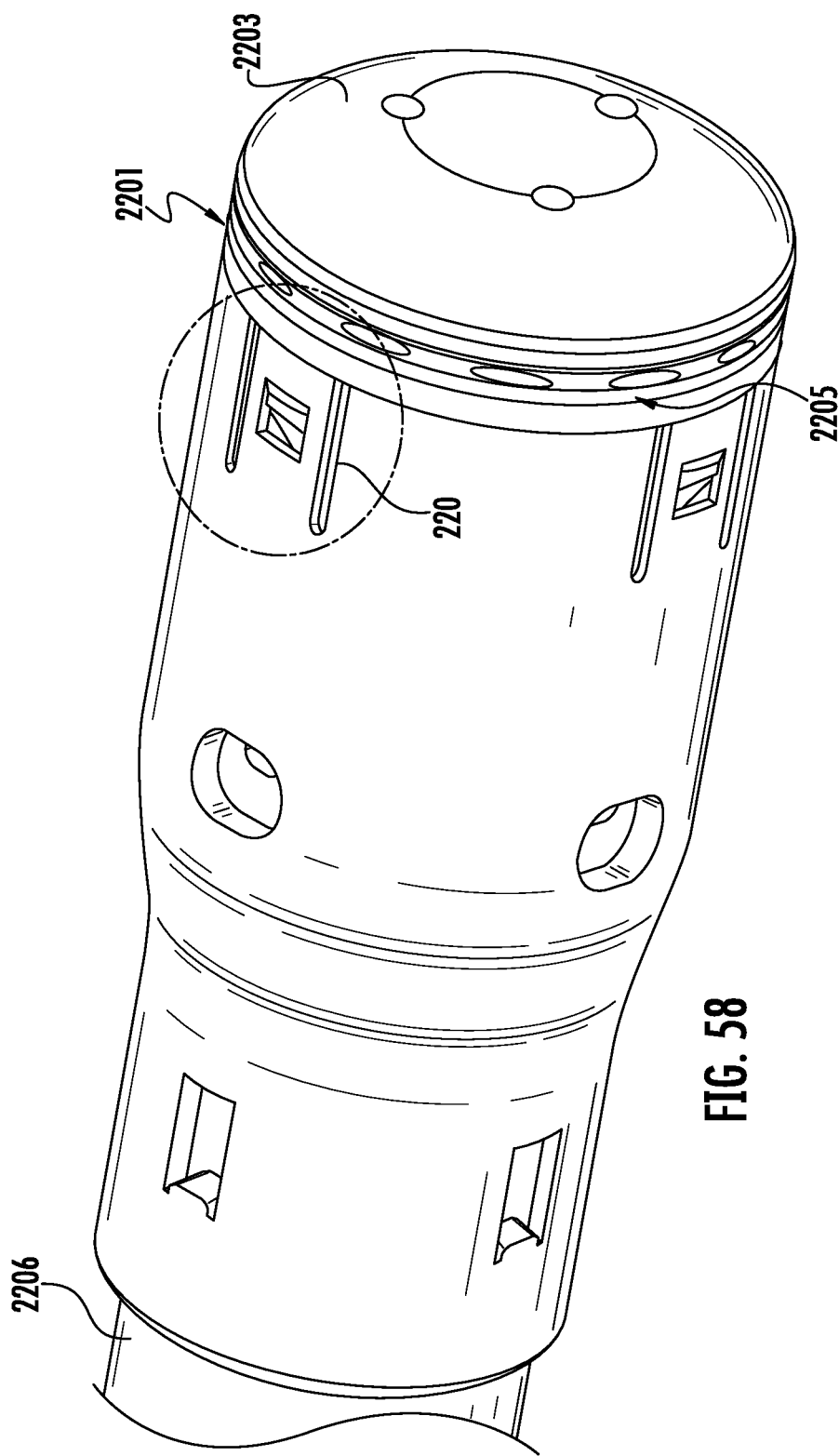
FIG. 58 is a perspective view of a circular loading unit attached to a shaft.

In the surgical system, the loading units can be different types of surgical stapling loading units, with corresponding adapters for adapting the output of the motor in the handle to the particular loading unit. For example, one type of loading unit is a circular stapling loading unit 2201. See FIG. 58. In contrast to the loading unit 116 discussed above, the anvil 2203 of the loading unit 2201 moves toward and away from a staple cartridge assembly 2205 while maintaining the tissue contacting surfaces thereof in a parallel relationship. A rod is advanced and retracted to accomplish the movement of the anvil 2203. A separate actuator is present to accomplish the firing of staples and cutting of tissue. By contrast, the dynamic clamping member discussed above accomplishes the clamping of the tool assembly onto tissue, and also the firing of staples. An appropriate adapter (not shown) is provided so that the loading unit 2201 can be used with a handle assembly like handle assembly 112 discussed above. The adapter has a shaft 2206 which may be curved, and cables, linkages, and/or bars, or combinations thereof, to space the anvil 2203 from the staple cartridge component 2205 so that the surgeon can dispose tubular sections of tissue around the anvil and cartridge component/assembly.

As is well known, the anvil can be approximated with the cartridge assembly and staples can be fired through the tissue. Subsequently, a circular knife cuts the tissue inwardly of the staple line.

Figure 60:
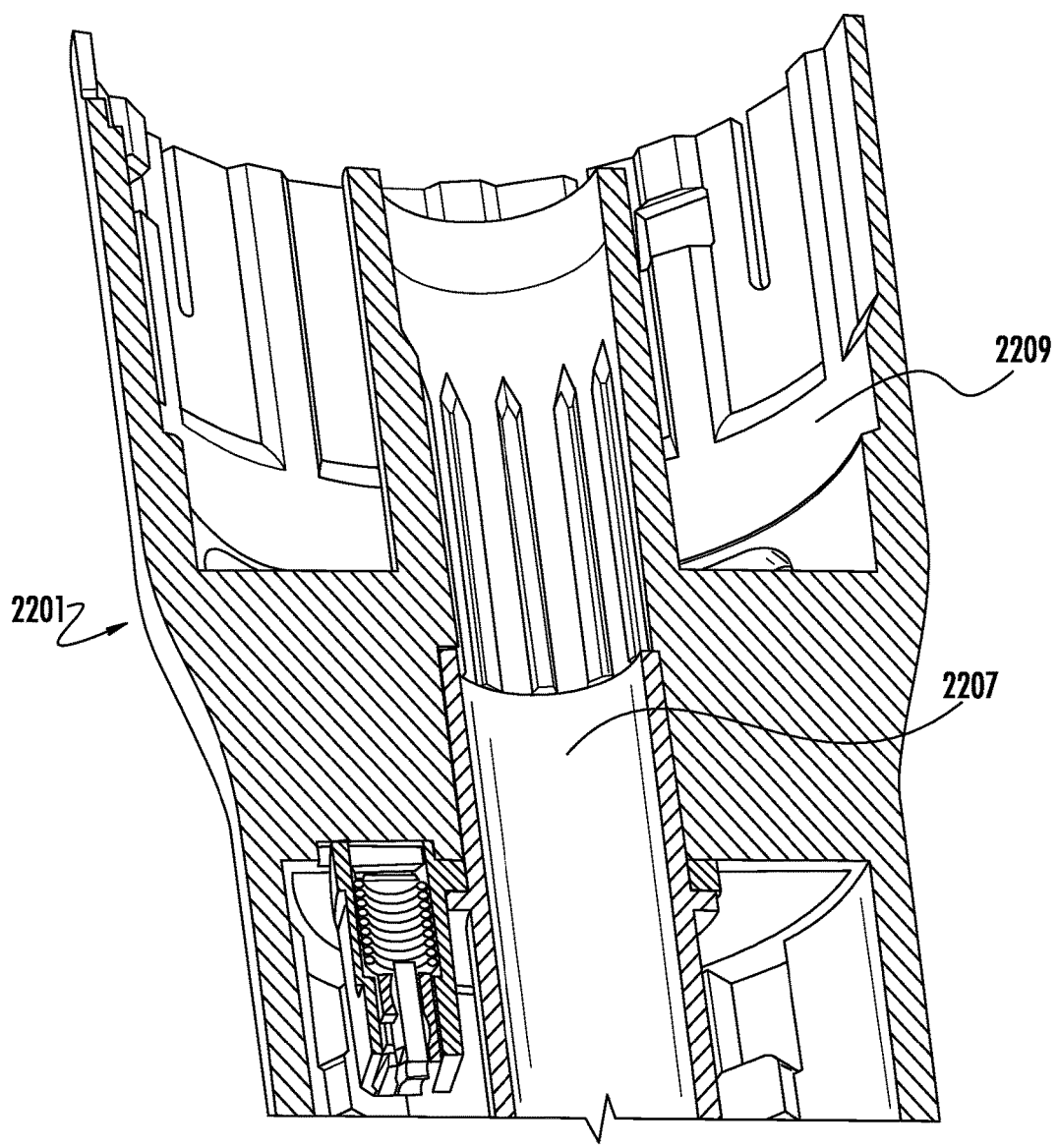
FIG. 60 is a cross sectional perspective view of the interior of the loading unit of FIG. 58 with parts removed.

For example, the loading unit 2201 can have a passage 2207 for a rod that connects to the actuator in the adapter, the actuator in the adapter (e.g., linkage, cable, rod, etc.) is driven by the powered (e.g., motorized) output of the handle assembly. See FIG. 60. It is the rod that moves the anvil 2203 as discussed above. The loading unit also has, as shown in FIG. 60, a space 2209 for receipt of a staple cartridge assembly or, alternatively the loading unit can have a staple cartridge that is permanently attached. The loading unit 2201 further has a staple pusher for firing staples and a knife for cutting tissue.

Accordingly, it may be desirable to use the controller of the surgical system to change the functionality of the various actuators on the handle assembly. For example, handle assembly 112 can have push buttons, rocker switches, touch screen features, and/or actuators of another type (generally called herein "buttons"). At least four such buttons are provided to: initiate articulation of an articulating loading unit, like loading unit 116; initiate the clamping of tissue, initiate the firing of staples; and initiate the cutting of tissue. In certain embodiments, there is a first button for articulation, and a second button for clamping and firing. A controller is provided, preferably in a powered (e.g., motorized) handle assembly, to change the function of the second button to clamping, firing and cutting when there is a linear surgical stapling reload like loading unit 16 or loading unit 116. The controller can be programmed to also change the function of the second actuator to clamping, allow use of the third actuator to initiate firing, and allow use of the fourth actuator to initiate cutting if the loading unit is a circular stapling loading unit like unit 2201. In certain embodiments, the controller is programmed to allow or prevent use of a button for initiating articulation of a tool assembly of a linear stapling loading unit, like loading unit 16 discussed above. In any of the embodiments disclosed herein, a controller of a handle assembly (or another component of the surgical system) can be programmed to change the function of one or more buttons, allow use of a button for a function, and/or prevent use of a button for a function.

Figure 59:
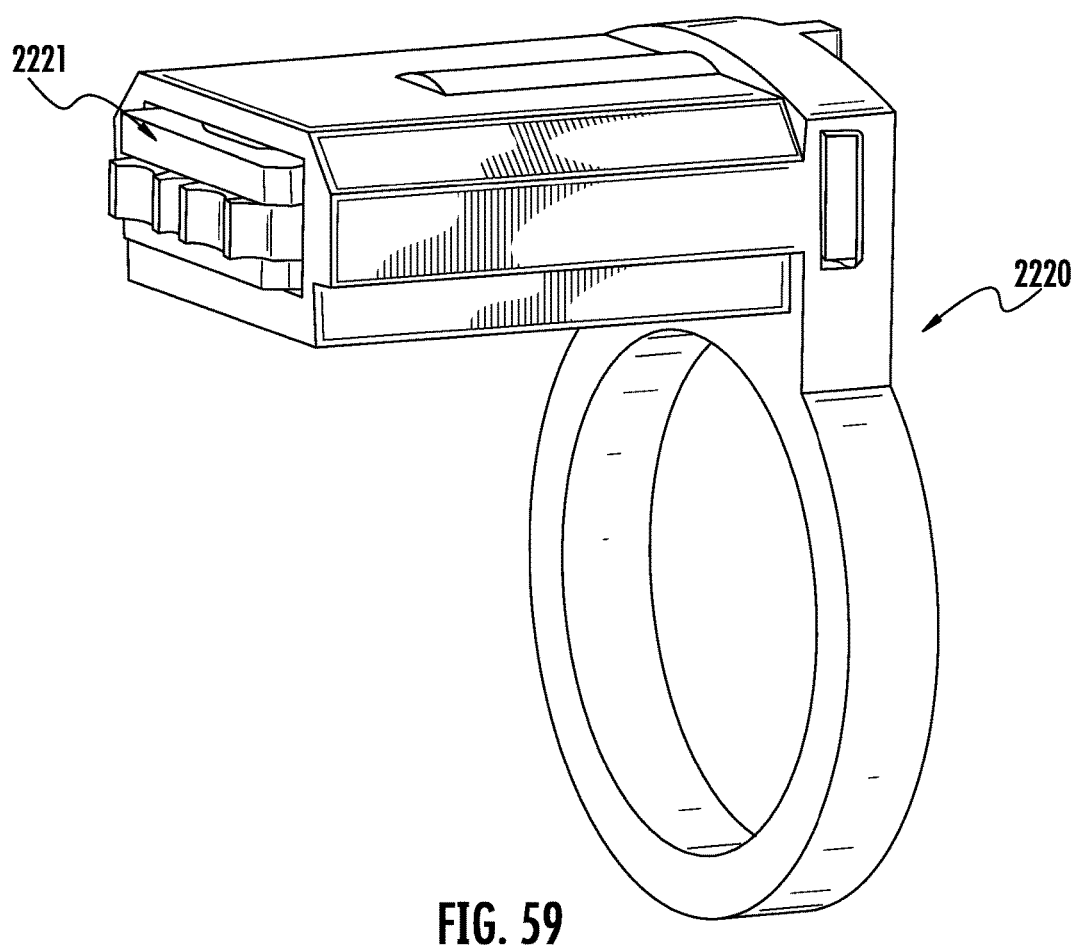
FIG. 59 is a perspective view of a chip assembly.

The circular stapling loading unit 2201 can include, as seen in FIG. 59, a chip assembly 2220 having a chip 2221, which may be as described above in connection with FIGS. 1 through 57. In addition, in certain embodiments, the unit 2201 has a removable and replaceable cartridge assembly (not shown) having its own chip assembly and chip.

Figure 61:
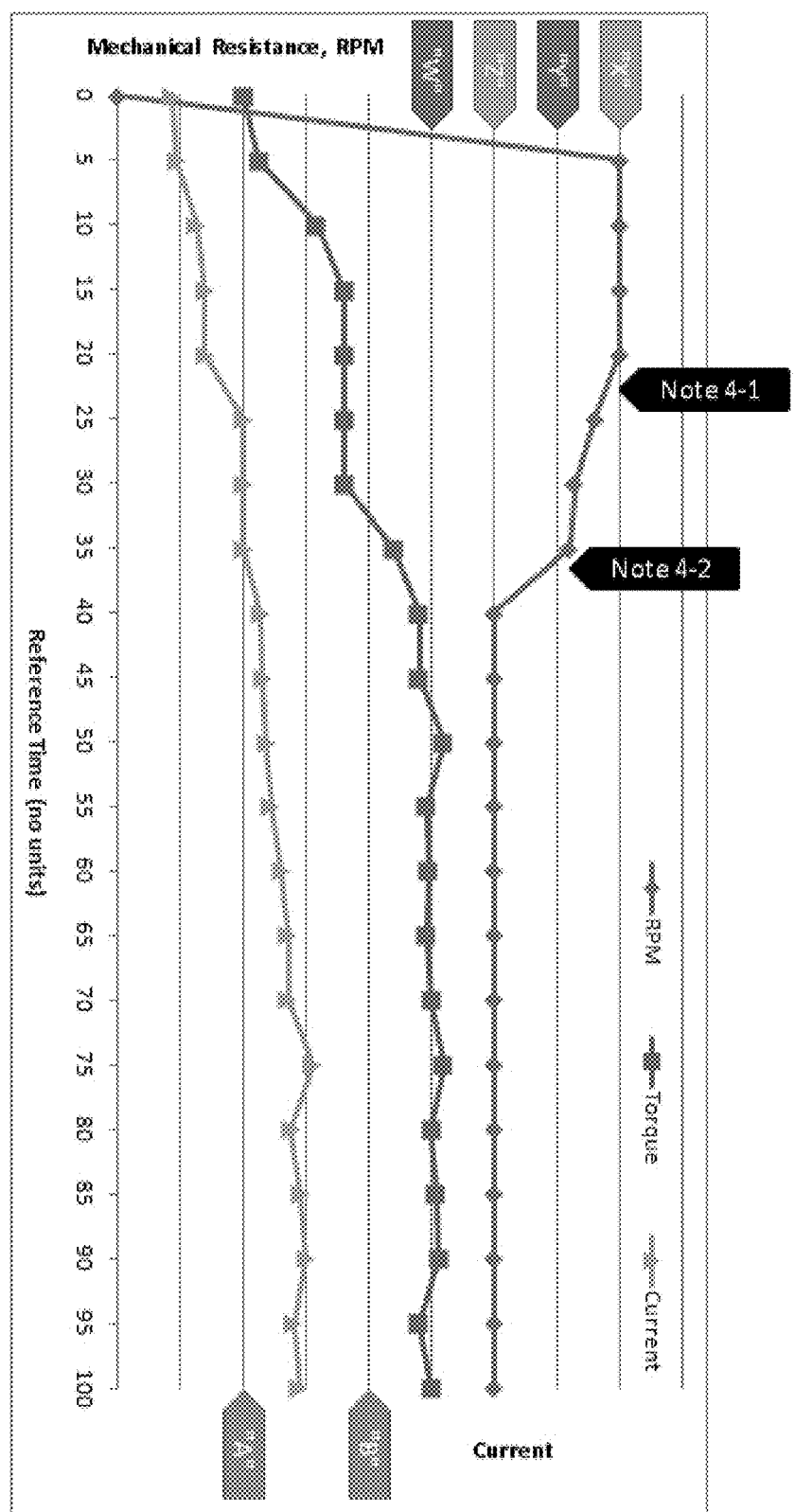
FIG. 61 is a graphical representing of a current profile in accordance with the present disclosure.

It is desirable that the controller programming and/or memory includes information concerning the potential end stops, or other important locations, for the potential loading units. For example, the linear stapling loading units may be 30 mm, 45 mm and/or 60 mm staple line units, so that the controller can be programmed to store information about the forces detected in various sensors and/or encoders when the drive assembly is at those locations. It is contemplated that any location for a movable part in the system that is of interest can be used, in any of the embodiments disclosed herein. If the appropriate sensors are provided on the particular loading unit, such as a pulse oximeter, temperature meter, etc., information concerning the condition of the tissue and/or surrounding site can be stored by the controller, the chips in the various components, and/or other computer components. Because there are various types of surgical loading units that are contemplated, such as stapling, electrosurgical, etc., and they can be provided in various configurations, such as different staple line lengths or diameters, staple sizes, levels of energy, etc., it is contemplated that there is a current profile associated with each. For example, the current read by a current meter or ammeter in the handle assembly during use of the loading unit over time can be read and saved. It is contemplated that the controller saves this current profile along with the identification code and type of loading unit, for example. This information can be compared with a known current profile by the controller, or another component in the surgical system. Inferences may be made concerning the firing of staples, the condition of tissue, the condition of the loading unit or other components in the system that were used, thick tissue, etc. In any of the embodiments disclosed herein, a current profile can be used and/or stored in the system as discussed above. For example, FIG. 61 illustrates a graphical representation of such a profile. The current begins to be limited at "A"; as the mechanical load increases RPM decreases. Once RPM decreases below a set limit, "Y", the device switches into a second mode. This mode increases the current limit to "B" and changes the desired RPM from "X" to "Z". This RPM change provides visual and audible feedback to the user.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A surgical system, comprising:
   a handle assembly having a controller, the controller having at least one program and a memory;
   an adapter assembly extending from the handle assembly; and
   a loading unit releasably secured to the adapter assembly, the loading unit having a tool assembly mounted for articulation and a member for actuating articulation of the tool assembly, the tool assembly including a removable and replaceable staple cartridge assembly, the loading unit having at least one chip assembly disposed within the staple cartridge assembly, the chip assembly having a chip storing data indicating a position of the member when the tool assembly is in a fully articulated position, wherein the chip receives information from the controller.

2. The surgical system according to claim 1, wherein the chip has data indicating a type of loading unit, the memory of the controller having a current profile for the type of loading unit.

3. The surgical system according to claim 1, wherein the chip stores data indicating a length of the tool assembly.

4. The surgical system according to claim 1, wherein the controller monitors current from a motor during operation of the loading unit.

5. The surgical system according to claim 1, wherein the removable and replaceable staple cartridge assembly has a chip assembly including a chip storing data indicating whether or not the staple cartridge assembly has been fired.

6. The surgical system according to claim 1, wherein the controller monitors the position of the member and stores data concerning movement of the member in the memory.

7. The surgical system according to claim 6, wherein the number of times the tool assembly has been articulated is saved in the memory.

8. The surgical system according to claim 6, wherein the memory has data indicating the position of the member when the tool assembly is in a fully articulated position.

9. A surgical system, comprising:
- a handle assembly having a controller, the controller having a memory and at least one program, the memory of the controller storing a plurality of current profiles;
- an adapter assembly extending from the handle assembly; and
- a loading unit releasably securable to the adapter assembly, the loading unit having a tool assembly including a removable and replaceable staple cartridge assembly, the removable and replaceable staple cartridge assembly including a chip, wherein the controller is configured to read a type of staple cartridge assembly from the chip and select a current profile from the plurality of current profiles stored in the controller, wherein the controller writes information to the chip.

10. The surgical system according to claim 9, wherein the controller stores information from sensors, encoders, or both.

11. The surgical system according to claim 10, wherein the controller compares the current profile to information from the sensors, encoders, or both.

12. The surgical system according to claim 9, wherein the chip stores data indicating whether or not the removable and replaceable staple cartridge assembly has been fired.

13. The surgical system according to claim 9, wherein the chip stores data indicating the length of the removable and replaceable staple cartridge assembly.

14. The surgical system according to claim 9, wherein the chip stores data indicating the staple configuration of the removable and replaceable staple cartridge assembly.

* * * * *